US007820805B2

(12) United States Patent (10) Patent No.: US 7,820,805 B2
Thomae et al. (45) Date of Patent: Oct. 26, 2010

(54) SULFOTRANSFERASE 2B1 PHARMACOGENETICS

(75) Inventors: Bianca A. Thomae, Chicago, IL (US); Eric D. Wieben, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 232 days.

(21) Appl. No.: 11/861,065

(22) Filed: Sep. 25, 2007

(65) Prior Publication Data

US 2008/0118975 A1 May 22, 2008

Related U.S. Application Data

(62) Division of application No. 10/702,981, filed on Nov. 6, 2003, now Pat. No. 7,288,642.

(60) Provisional application No. 60/424,420, filed on Nov. 7, 2002.

(51) Int. Cl.
*C07H 21/02* (2006.01)
*C07H 21/04* (2006.01)
*C12P 19/34* (2006.01)
*C12Q 1/68* (2006.01)

(52) U.S. Cl. ............... 536/23.1; 536/24.3; 435/91.1; 435/91.2; 435/6

(58) Field of Classification Search ............ None
See application file for complete search history.

(56) References Cited

U.S. PATENT DOCUMENTS

| | | | |
|---|---|---|---|
| 5,541,308 A * | 7/1996 | Hogan et al. ............... | 536/23.1 |
| 5,733,729 A | 3/1998 | Lipshutz et al. | |
| 5,770,722 A | 6/1998 | Lockhart et al. | |
| 6,110,709 A * | 8/2000 | Ausubel et al. ............ | 435/91.2 |
| 6,242,244 B1 | 6/2001 | Donohue et al. | |
| 6,747,137 B1 * | 6/2004 | Weinstock et al. ......... | 536/23.1 |
| 2001/0036632 A1 * | 11/2001 | Yu et al. ..................... | 435/6 |
| 2003/0084474 A1 * | 5/2003 | Sung et al. ................. | 800/278 |
| 2009/0093620 A1 * | 4/2009 | Kovalic et al. ............. | 536/23.1 |

FOREIGN PATENT DOCUMENTS

WO  WO 02/68579  6/2002

OTHER PUBLICATIONS

Campbell et al., "Human Liver Phenol Sulfotransferase: Assay Conditions, Biochemical Properties and Partial Purification of Isozymes of the Thermostable Form," *Biochem. Pharmacol.*, 1987, 36(9):1435-1446.
Chin, "On the preparation and utilization of isolated and purified oligonucleotides," University of North Carolina, Mar. 9, 2002.
Cibelli et al., "Cloned Transgenic Calves Produced from Nonquiescent Fetal Fibroblasts," *Science*, 1998, 280:1256-1258.
Cleland, "Computer Programmes for Processing Enzyme Kinetic Data," *Enzyme*, 1963, 198:463-465.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Excoffier and Slatkin, "Maximum-Likelihood Estimation of Molecular Haplotype Frequencies in a Diploid Population," *Mol. Biol. Evol.*, 1995, 12(5):921-927.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nature Genet.*, 1996, 14:441-447.
Halushka et al., "Patterns of single-nucleotide polymorphisms in candidate genes for blood-pressure homeostasis," *Nat. Genet.*, 1999, 22:239-247.
Hartl and Clark, "Chromosomes and Heredity," *Principles of Population Genetics*, $3^{rd}$ ed., 1997, Sinauer Associates, Inc., (Sunderland, MA), pp. 96-106.
Hedrick, "An Introduction to Gametic Disequilibrium," *Genetics of Populations*, $2^{nd}$ ed., 2000, Jones and Bartlett, (Sudbury, MA), pp. 396-406.
Her et al., "Human hydroxysteroid sulfotransferase SULT2B1: two enzymes encoded by a single chromosome 19 gene," *Genomics*, 1998, 53:284-295.
Ho et al., "Site-directed mutagenesis by overlap extension using the polymerase chain reaction," *Gene*, 1989, 77:51-59.
Hyrup and Nielsen, "Peptide Nucleic Acids (PNA): Synthesis, Properties and Potential Applications," *Bioorgan. Med. Chem.*, 1996, 4(1):5-23.
Iida et al., "Catalog of 320 single nucleotide polymorphisms (SNPs) in 20 quinone oxidoreductase and sulfotransferase genes," *J. Hum. Genet.*, 2001, 46:225-240.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.
Lewis, "PCR's Competitors Are Alive and Well and Moving Rapidly Towards Commercialization," *Genetic Engineering News*, 1992, vol. 12, 3 pages.
Long et al., "An E-M Algorithm and Testing Strategy for Multiple-Locus Haplotypes," *Am. J. Hum. Genet.*, 1995, 56:799-810.

(Continued)

*Primary Examiner*—Sarae Bausch
*Assistant Examiner*—Katherine Salmon
(74) *Attorney, Agent, or Firm*—Fish & Richardson P.C.

(57) ABSTRACT

Isolated sulfotransferase nucleic acid molecules that include a nucleotide sequence variant and nucleotides flanking the sequence variant are described, as are sulfotransferase allozymes. Methods for determining the sulfonator status of a subject also are described. In addition, methods for predicting the therapeutic efficacy of a compound in a subject are described, as are methods for estimating the dose of a compound to be administered to a subject.

12 Claims, 15 Drawing Sheets

OTHER PUBLICATIONS

Myakishev et al., "High-Throughput SNP Genotyping by Allele-Specific PCR with Universal Energy-Transfer-Labeled Primers," *Genome Res.*, 2001, 11:163-169.

Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.

Schafer and Hawkins, "DNA variation and the future of human genetics," *Nat. Biotechnol.*, 1998, 16:33-39.

Shastry, "Gene disruption in mice: Models of development and disease," *Mol. Cell Biochem.*, 1998, 181:163-179.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug. Dev.*, 1997, 7:187-195.

Terwilliger and Ott, *Handbook of Human Genetic Linkage*, 1994, The Johns Hopkins University Press, Baltimore, pp. 188-193.

Underhill et al., "Detection of Numerous Y Chromosome Biallelic Polymorphisms by Denaturing High-Performance Liquid Chromatography," *Genome Res.*, 1997, 7:996-1005.

Van Loon and Weinshilboum, "Thiopurine Methyltransferase Isozymes in Human Renal Tissue," *Drug Metab. Dispos.*, 1990, 18(5):632-638.

Van Loon et al., "Human Kidney Thiopurine Methyltransferase. Photoaffinity Labeling with S-Adenosyl-$_L$-Methionine," *Biochem. Pharmacol.*, 1992, 44(4):775-785.

Wakayama et al., "Full-term development of mice from enucleated oocytes injected with cumulus cell nuclei," *Nature*, 1998, 394:369-374.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Wilmut et al., "Viable offspring derived from fetal and adult mammalian cells," *Nature*, 1997, 385:810-813.

Wood et al., "Human Liver Thermolabile Phenol Sulfotransferase: cDNA Cloning, Expression and Characterization," *Biochem. Biophys. Res. Comm.*, 1994, 198(3):1119-1127.

\* cited by examiner

Figure 1

Exon 1b

```
        GTCTCCGCCCTCCGTGTATCTCTGTTGCGTCTCTCAAGGTCTGTGGCCCCTGTGCATCTC
  1     ---------+---------+---------+---------+---------+---------+    60
        CAGAGGCGGGAGGCACATAGAGACAACGCAGAGAGTTCCAGACACCGGGGACACGTAGAG

AGTCCCCTCCTGGTATCTGTCTCCCATGCCCTCTGCCCTCTCCCTTTCTCCCTGGCTCCC
 61     ---------+---------+---------+---------+---------+---------+   120
        TCAGGGGAGGACCATAGACAGAGGGTACGGGAGACGGGAGAGGGAAAGAGGGACCGAGGG

GCCCTGTCTGTGCTGCCGTGGTCCTGGCTGTGCCTCTGTCCCTGTGTCTGTTTCCAGGGT
121     ---------+---------+---------+---------+---------+---------+   180
        CGGGACAGACACGACGGCACCAGGACCGACACGGAGACAGGGACACAGACAAAGGTCCCA

GCCCCTTACGCGTCAGCCCGTGAGGGCAAGTTTCTGTCTGCCCCTTCCCCAGCGGTGGCC
181     ---------+---------+---------+---------+---------+---------+   240
        CGGGGAATGCGCAGTCGGGCACTCCCGTTCAAAGACAGACGGGGAAGGGGTCGCCACCGG

TAGTGCTTGGAACAGCGCCTGGCAGACAGGAGATGCTCAGTAAATATTTCTCAAATGAAT
241     ---------+---------+---------+---------+---------+---------+   300
        ATCACGAACCTTGTCGCGGACCGTCTGTCCTCTACGAGTCATTTATAAAGAGTTTACTTA

AAAGGAATGAATGAGTGAATGAATGAATGAATGAATGAACTCGCTGAGATGGGCGAGATC
301     ---------+---------+---------+---------+---------+---------+   360
        TTTCCTTACTTACTCACTTACTTACTTACTTACTTACTTGAGCGACTCTACCCGCTCTAG

AGCGCCATTTCCCAAATGAGCAACGTGGGCTCCAGGTGGGTGCCCACAGGCCCAGAACTG
361     ---------+---------+---------+---------+---------+---------+   420
        TCGCGGTAAAGGGTTTACTCGTTGCACCCGAGGTCCACCCACGGGTGTCCGGGTCTTGAC

CCAGCCCGGAAGGTTCTGGCGTGGGTTTGGCACTGACCCCATGGATTCTGCCCCCAGCTG
421     ---------+---------+---------+---------+---------+---------+   480
        GGTCGGGCCTTCCAAGACCGCACCCAAACCGTGACTGGGGTACCTAAGACGGGGTCGAC

AGCACCAGACGCCAGGACGTGCCCATCACTGCTCCTCCCCGCCCTCAGAACAGGGTGGCT
481     ---------+---------+---------+---------+---------+---------+   540
        TCGTGGTCTGCGGTCCTGCACGGGTAGTGACGAGGAGGGGCGGGAGTCTTGTCCCACCGA

CCCTCTGGCCTCTCCCCGCTGTTGGAGGCGTGGGTAGCAGCTGGGAGAACCGGCTGGGTG
541     ---------+---------+---------+---------+---------+---------+   600
        GGGAGACCGGAGAGGGCGACAACCTCCGCACCCATCGTCGACCCTCTTGGCCGACCCAC

CTGCCCCTCCCCTTGGGCCGGGCACGGAGTAGGCACCTGGCGGGCTCCCCAGGTGGC|AGA
601     ---------+---------+---------+---------+---------+---------+   660
        GACGGGGAGGGGAACCCGGCCCGTGCCTCATCCGTGGACCGCCCGAGGGGTCCACCG|TCT

CGCTGTCGCTGCGCACACCTGGCCTCTGTGCCGCCTGCTCCCTGCTCGTCCTCCCT[C]CC
661     ---------+---------+---------+---------+---------+---------+   720
        GCGACAGCGACGCGTGTGGACCGGAGACACGGCGGACGAGGGACGAGCAGGAGGGGAGGG

CACCCTCACCCACCTGCCATGGACGGGCCCGC[C]GAGCCCCAGATCCCGGGCTTGTGGGAC
721     ---------+---------+---------+---------+---------+---------+   780
        GTGGGAGTGGGTGGACGGTACCTGCCCGGGCGGCTCGGGGTCTAGGGCCCGAACACCCTG

M  D  G  P  A  E  P  Q  I  P  G  L  W  D  -
```

Figure 1 – page 2

```
         ACCTATGAAGATGACATCTCGGAAATCAGGTGAGGCCCAGACCTGGGCAGGAGCCAGGAG
    781  ---------+---------+---------+---------+---------+---------+  840
         TGGATACTTCTACTGTAGAGCCTTTAGTCCACTCCGGGTCTGGACCCGTCCTCGGTCCTC

T  Y  E  D  D  I  S  E  I (amino acid residues 1-23 of SEQ ID NO:18)

ATCCCAGGGAGGAGGTGGCTGTTTGGGGGAGCCGGGGACTGTGGCAAGGGTGGCCTCCAG
    841  ---------+---------+---------+---------+---------+---------+  900
         TAGGGTCCCTCCTCCACCGACAAACCCCCTCGGCCCCTGACACCGTTCCCACCGGAGGTC

CCACCCGCAGCCGCAGGCCTGGCCCAGACTTAGCTGGAGGGGCTGGGCTGGGCTGGGGCA
    901  ---------+---------+---------+---------+---------+---------+  960
         GGTGGGCGTCGGCGTCCGGACCGGGTCTGAATCGACCTCCCCGACCCGACCCGACCCCGT
                                                                ‾‾‾‾‾‾‾‾

TCCAGTGTG      (SEQ ID NO:1)
    961  ---------  969
         AGGTCACAC      (SEQ ID NO:2)
         ‾‾‾‾‾‾‾‾‾
```

Exon 1a

```
         AGGATGAGAGCCAGGTTCATTGAATTCCAAAGAGGCTGGGAAAGAAGAGGGTGTATTAAC
         ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
      1  ---------+---------+---------+---------+---------+---------+  60
         TCCTACTCTCGGTCCAAGTAACTTAAGGTTTCTCCGACCCTTTCTTCTCCCACATAATTG

TGAGCACTTGCTGTGTGCCAGGATTCATGCTCAGTGCTTGCTTGCTTTTATTTTTTTGAG
     61  ---------+---------+---------+---------+---------+---------+  120
         ACTCGTGAACGACACACGGTCCTAAGTACGAGTCACGAACGAACGAAAATAAAAAAACTC

ACGGAGTCTCTCACTCTGTCACCCAGGCTGGAGTGCAGTGG|CGTGATCTCAGCTCACTGC
    121  ---------+---------+---------+---------+---------+---------+  180
         TGCCTCAGAGAGTGAGACAGTGGGTCCGACCTCACGTCACC|GCACTAGAGTCGAGTGACG

AGCTTCTGCTTCCCAGCTTCAAGCGATTCTCGTAACTCAGCCTCCCGAGTGGCTGGGACT
    181  ---------+---------+---------+---------+---------+---------+  240
         TCGAAGACGAAGGGTCGAAGTTCGCTAAGAGCATTGAGTCGGAGGGCTCACCGACCCTGA

GCAGGCGCATGCAACCACATCTGGCTAATTTTTGTCTTTTTAGTAGAGACAGGGTTTCAC
    241  ---------+---------+---------+---------+---------+---------+  300
         CGTCCGCGTACGTTGGTGTAGACCGATTAAAAACAGAAAAATCATCTCTGTCCCAAAGTG

CATGTTGGCCAGGCTGGTCTCAAACTCCTGACCTCAGGTGATCCACCCACCT[C]TGTCTCC
    301  ---------+---------+---------+---------+---------+---------+  360
         GTACAACCGGTCCGACCAGAGTTTGAGGACTGGAGTCCACTAGGTGGGTGGAGACAGAGG

CAAAGTGCTGGGATTACAGGAGTGTGCCACTGCGCCTGACCAGCTTTATAAAGTTTATAG
                                                                    ‾
    361  ---------+---------+---------+---------+---------+---------+  420
         GTTTCACGACCCTAATGTCCTCACACGGTGACGCGGACTGGTCGAAATATTTCAAATATC
         ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾

GGACAGTGTCACCACTTTACAGAAGAGGGACTGAGGCTCTGAGGAGGAAGTTCCTTGCCA
         ‾‾‾‾‾‾‾‾‾‾‾‾‾‾‾‾‾‾‾‾‾‾‾‾‾‾‾‾‾‾
    421  ---------+---------+---------+---------+---------+---------+  480
         CCTGTCACAGTGGTGAAATGTCTTCTCCCTGACTCCGAGACTCCTCCTTCAAGGAACGGT
```

Figure 1 – page 3

```
     GGGTCCGAGTGTCGCCACCCTGAGAACTCCAGCACCCACCTCCCTACTCTCCCTCATGGC
481  ---------+---------+---------+---------+---------+---------+ 540
     CCCAGGCTCACAGCGGTGGGACTCTTGAGGTCGTGGGTGGAGGGATGAGAGGGAGTACCG

M  A  -

GTCTCCCCCACCTTTCCACAGCCAGAAGTTGCCAGGTGAATACTTCCGGTACAAGGGCGT
541  ---------+---------+---------+---------+---------+---------+ 600
     CAGAGGGGGTGGAAAGGTGTCGGTCTTCAACGGTCCACTTATGAAGGCCATGTTCCCGCA

S  P  P  P  F  H  S  Q  K  L  P  G  E  Y  F  R  Y  K  G  V  -

CCCCTTCCCCGTCGGCCTGTACTCGCTCGAGAGCATCAGCTTGGCGGAGAACACCCAAGA
601  ---------+---------+---------+---------+---------+---------+ 660
     GGGGAAGGGGCAGCCGGACATGAGCGAGCTCTCGTAGTCGAACCGCCTCTTGTGGGTTCT

P  F  P  V  G  L  Y  S  L  E  S  I  S  L  A  E  N  T  Q  D  -

TGTGCGGGACGACGACATCTTTATCATCACCTACCCCAAGTCAGGTACCTGCCGGGCTGC
661  ---------+---------+---------+---------+---------+---------+ 720
     ACACGCCCTGCTGCTGTAGAAATAGTAGTGGATGGGGTTCAGTCCATGGACGGCCCGACG

V  R  D  D  D  I  F  I  I  T  Y  P  K  S  G  (amino acid residues
                                                       1-57 of SEQ ID NO:16)

GGGCGTCGGGGGCTGGGGAGAGTGGGGAGGGGGTGCGGCAGAGGACAGGAAAGGCACATA
721  ---------+---------+---------+---------+---------+---------+ 780
     CCCGCAGCCCCCGACCCCTCTCACCCCTCCCCACGCCGTCTCCTGTCCTTTCCGTGTAT

GAGAAGGAGGGGAGGAGGAAAAGTGGGGCCGGGTCTGTT    (SEQ ID NO:3)
781  ---------+---------+---------+---------   819
     CTCTTCCTCCCCTCCTCCTTTTCACCCCGGCCCAGACAA     (SEQ ID NO:4)
```

Exon 2

```
     AGCCTGGGCGACAGAGTAAGACTCTGTCTTAAAAAAAATAATAAAAGGTGGCAAATTGCT
  1  ---------+---------+---------+---------+---------+---------+ 60
     TCGGACCCGCTGTCTCATTCTGAGACAGAATTTTTTTTATTATTTTCCACCGTTTAACGA

CAATAAGTGCTGTTGTGATTATTCTGATGATATCTCCCTCTTCAGCCCTCCCACACCCAA
 61  ---------+---------+---------+---------+---------+---------+ 120
     GTTATTCACGACAACACTAATAAGACTACTATAGAGGGAGAAGTCGGGAGGGTGTGGGTT

TTAATCTGCTCGTTTCTCCCAACAGGCACGACCTGGATGATCGAGATCATCTGCTTAATC
121  ---------+---------+---------+---------+---------+---------+ 180
     AATTAGACGAGCAAAGAGGGTTGTCCGTGCTGGACCTACTAGCTCTAGTAGACGAATTAG

T  T  W  M  I  E  I  I  C  L  I  -
```

Figure 1 – page 4

```
        CTGAAGGAAGGGGATCCATCCTGGATCCGCTCCGTGCCCATCTGGGAGCGGGCACCCTGG
  181   ---------+---------+---------+---------+---------+---------+ 240
        GACTTCCTTCCCCTAGGTAGGACCTAGGCGAGGCACGGGTAGACCCTCGCCCGTGGGACC

L   K   E   G   D   P   S   W   I   R   S   V   P   I   W   E   R   A   P   W   -

TGTGAGACCATTGTGGGTGCCTTCAGCCTCCCGGACCAGTACAGCCCCCGCCTCATGAGC
  241   ---------+---------+---------+---------+---------+---------+ 300
        ACACTCTGGTAACACCCACGGAAGTCGGAGGGCCTGGTCATGTCGGGGCGGAGTACTCG

C   E   T   I   V   G   A   F   S   L   P   D   Q   Y   S   P   R   L   M   S   -

TCCCATCTTCCCATCCAGATCTTCACCAAGGCCTTCTTCAGCTCCAAGGCCAAGGTTGGG
  301   ---------+---------+---------+---------+---------+---------+ 360
        AGGGTAGAAGGGTAGGTCTAGAAGTGGTTCCGGAAGAAGTCGAGGTTCCGGTTCCAACCC

S   H   L   P   I   Q   I   F   T   K   A   F   F   S   S   K   A   K  (amino acid
                                                           residues 58-126 of SEQ ID NO:16)

AGGAGGGGTGTGTGTCAGTTGGGAGGGGCTGCATGGGTGTATGGGGTAATGGGGGGACGG
  361   ---------+---------+---------+---------+---------+---------+ 420
        TCCTCCCCACACACAGTCAACCCTCCCCGACGTACCCACATACCCCATTACCCCCCTGCC

AGCATAACTCATTGATTCATTCAGCACCTATTTGTTAAACACTTACTATGTGCCTGACTC
  421   ---------+---------+---------+---------+---------+---------+ 480
        TCGTATTGAGTAACTAAGTAAGTCGTGGATAAACAATTTGTGAATGATACACGGACTGAG

TGATCTAGCACAGTGGTCAATATACACACAGAAATGCCTGCCCTTTGGCAGGGA   (SEQ ID NO:5)
  481   ---------+---------+---------+---------+---------+----- 534
        ACTAGATCGTGTCACCAGTTATATGTGTGTCTTTACGGACGGGAAACCGTCCCT   (SEQ ID NO:6)
```

Exon 3

```
        AGGGGTCTCCAGGGCAGGAGGCCTCAGGGGCTGGGGTCTTGCCTGTGTCTGACGCCTTCT
    1   ---------+---------+---------+---------+---------+---------+ 60
        TCCCCAGAGGTCCCGTCCTCCGGAGTCCCCGACCCCAGAACGGACACAGACTGCGGAAGA

CCCCTCTCCTCACCATCCGCACACAGGTGATCTACATGGGCCGCAACCCCCGGGACGTTG
   61   ---------+---------+---------+---------+---------+---------+ 120
        GGGGAGAGGAGTGGTAGGCGTGTGTCCACTAGATGTACCCGGCGTTGGGGGCCCTGCAAC

V   I   Y   M   G   R   N   P   R   D   V   V   -

TGGTCTCCCTCTATCATTACTCCAAGATCGCCGGGCAGTTAAAGGACCCGGGCACACCCG
  121   ---------+---------+---------+---------+---------+---------+ 180
        ACCAGAGGGAGATAGTAATGAGGTTCTAGCGGCCCGTCAATTTCCTGGGCCCGTGTGGGC

V   S   L   Y   H   Y   S   K   I   A   G   Q   L   K   D   P   G   T   P   D   -

ACCAGTTCCTGAGGGACTTCCTCAAAGGCGAAGGTGGGGACAGGGTAAAGCGGGGCAGGA
  181   ---------+---------+---------+---------+---------+---------+ 240
        TGGTCAAGGACTCCCTGAAGGAGTTTCCGCTTCCACCCCTGTCCCATTTCGCCCCGTCCT

Q   F   L   R   D   F   L   K   G   E  (amino acid residues 127-168 of
                                                             SEQ ID NO:16)
```

Figure 1 – page 5

```
              GGGGTGGGGAGGAGCCCCAGAGGACCCTGATGGGCAGAGGGACAGAGGAGGGGTAAGAAA
        241   ---------+---------+---------+---------+---------+---------+ 300
              CCCCACCCCTCCTCGGGGTCTCCTGGGACTACCCGTCTCCCTGTCTCCTCCCCATTCTTT

GGGAGAGAGACAGAGACACAGGGCATCAAAAGGGGCAATAGAGACAGAGAGCAGGTGGCC
        301   ---------+---------+---------+---------+---------+---------+ 360
              CCCTCTCTCTGTCTCTGTGTCCCGTAGTTTTCCCCGTTATCTCTGTCTCTCGTCCACCGG

AGGAGAAGAAGAGACGGA     (SEQ ID NO:7)
        361   ---------+-------- 378
              TCCTCTTCTTCTCTGCCT     (SEQ ID NO:8)
```

Exon 4

```
              CCCAGTGGGGCTGGGGGAACCCGCCACTCAGCCCTCACCCCACTTGTCCCTCTGCCCACA
          1   ---------+---------+---------+---------+---------+---------+ 60
              GGGTCACCCCGACCCCCTTGGGCGGTGAGTCGGGAGTGGGGTGAACAGGGAGACGGGTGT

GTGCAGTTTGGCTCCTGGTTCGACCACATTAAGGGCTGGCTTCGGATGAAGGGCAAAGAC
         61   ---------+---------+---------+---------+---------+---------+ 120
              CACGTCAAACCGAGGACCAAGCTGGTGTAATTCCCGACCGAAGCCTACTTCCCGTTTCTG

V   Q   F   G   S   W   F   D   H   I   K   G   W   L   R   M   K   G   K   D   -

AACTTCCTATTTATCACCTACGAGGAGCTGCAGCAGGTGAGTCCCCACCTCCTCCAGGTG
        121   ---------+---------+---------+---------+---------+---------+ 180
              TTGAAGGATAAATAGTGGATGCTCCTCGACGTCGTCCACTCAGGGGTGGAGGAGGTCCAC

N   F   L   F   I   T   Y   E   E   L   Q   Q   (amino acid residues 169-200
                                                                      of SEQ ID NO:16)

CAGCGTCCCCCCCATACCTTCTGCTCACACCCCACACTCTCCCCTTCCCGAGGGTCTCAG
        181   ---------+---------+---------+---------+---------+---------+ 240
              GTCGCAGGGGGGGTATGGAAGACGAGTGTGGGGTGTGAGAGGGGAAGGGCTCCCAGAGTC

GACCCTTCCGCTTCCCCATGCAATGCGCCAGCCCCTGGGGATACTGCAGGAACAGAACAG
        241   ---------+---------+---------+---------+---------+---------+ 300
              CTGGGAAGGCGAAGGGGTACGTTACGCGGTCGGGGACCCCTATGACGTCCTTGTCTTGTC

AGGCCCTGAGCCTGTGAGCAAGACCACAGACAAAAT    (SEQ ID NO:9)
        301   ---------+---------+---------+------ 336   Reverse primer not in contig
              TCCGGGACTCGGACACTCGTTCTGGTGTCTGTTTTA    (SEQ ID NO:10)
```

Exon 5

```
              CTCAGGCAGCCCCAGGTTAGGACCCAGACATGCGGATCCCAGGTTCCACGCTCCTTCCTT
          1   ---------+---------+---------+---------+---------+---------+ 60
              GAGTCCGTCGGGGTCCAATCCTGGGTCTGTACGCCTAGGGTCCAAGGTGCGAGGAAGGAA

GGCCGAGTGCCCTCCCTCCGCTGGCCCCTCTCCCCTGCCTGCAGGACTTACAGGGCTCCG
         61   ---------+---------+---------+---------+---------+---------+ 120
              CCGGCTCACGGGAGGGAGGCGACCGGGGAGAGGGGACGGACGTCCTGAATGTCCCGAGGC

D   L   Q   G   S   V   -
```

Figure 1 – page 6

```
     TGGAGCGCATCTGTGGGTTCCTGGGCC[G]TCCGCTGGGCAAGGAGGCACTGGGCTCCGTCG
121  ---------+---------+---------+---------+---------+---------+ 180
     ACCTCGCGTAGACACCCAAGGACCCGGCAGGCGACCCGTTCCTCCGTGACCCGAGGCAGC

E   R   I   C   G   F   L   G  [R]  P   L   G   K   E   A   L   G   S   V   V   -

TGGCACACTCAACCTTCAGCGCCATGAAGGCCAACACCATGTCCAACTACACGCTGCTGC
181  ---------+---------+---------+---------+---------+---------+ 240
     ACCGTGTGAGTTGGAAGTCGCGGTACTTCCGGTTGTGGTACAGGTTGATGTGCGACGACG

A   H   S   T   F   S   A   M   K   A   N   T   M   S   N   Y   T   L   L   P   -

CTCCCAGCCTGCTGGACCACCGTCGCGGGGCCTTCCTCCGGAAAGG[T][G]CGGGGGTTCTGG
241  ---------+---------+---------+---------+---------+---------+ 300
     GAGGGTCGGACGACCTGGTGGCAGCGCCCCGGAAGGAGGCCTTTCCACGCCCCCAAGACC

P   S   L   L   D   H   R   R   G   A   F   L   R   K   G    (amino acid residues
                                                                      201-261 of SEQ ID NO:16)

GGTTCAGAGCCCACTAGGCCACTGCCCGGCTGTGTGACCTGGGAGAGTTACTTAACCTCT
301  ---------+---------+---------+---------+---------+---------+ 360
     CCAAGTCTCGGGTGATCCGGTGACGGGCCGACACACTGGACCCTCTCAATGAATTGGAGA

CTGGGCCTCAGTTTCTCACCCAGCTGTAACATTGGGTGAACAGGG    (SEQ ID NO:11)
361  ---------+---------+---------+---------+-----  405
     GACCCGGAGTCAAAGAGTGGGTCGACATTGTAACCCACTTGTCCC    (SEQ ID NO:12)
```

Exon 6

```
     GGACGGTGTTTCTGGCAAAGGGAACACCTCGCCAAAGGCCGGGAAGGGGAAGGAGGTTGC
  1  ---------+---------+---------+---------+---------+---------+ 60
     CCTGCCACAAAGACCGTTTCCCTTGTGGAGCGGTTTCCGGCCCTTCCCCTTCCTCCAACG

TGGAATGTTGGAGGTAGGGGCGCAGTGCTCCCCAGAGGCTCCTCACCCCCTGGTGCCCCC
 61  ---------+---------+---------+---------+---------+---------+ 120
     ACCTTACAACCTCCATCCCCGCGTCACGAGGGGTCTCCGAGGAGTGGGGGACCACGGGGG

TCTTCTCCAGGGGTCTC[T]GGCGACTGGAAGAACCACTTCACGGTGGCCCAGAGCGAAGCC
121  ---------+---------+---------+---------+---------+---------+ 180
     AGAAGAGGTCCCCAGACACCGCTGACCTTCTTGGTGAAGTGCCACCGGGTCTCGCTTCGG

V   C   G   D   W   K   N   H   F   T   V   A   Q   S   E   A   -

TTCGATCGTGCCTACCGCAAGCAGATGCGGGGGATGCCGACCTTCCCCTGGGATGAAGAC
181  ---------+---------+---------+---------+---------+---------+ 240
     AAGCTAGCACGGATGGCGTTCGTCTACGCCCCCTACGGCTGGAAGGGGACCCTACTTCTG

F   D   R   A   Y   R   K   Q   M   R   G   M   P   T   F   P   W   D   E   D   -

CCGGAGGAGGA[C]GGCAGCCCAGATCCTGAGCCCAGCCCTGAGCCTGAGCCCAAGCCCAGC
241  ---------+---------+---------+---------+---------+---------+ 300
     GGCCTCCTCCTGCCGTCGGGTCTAGGACTCGGGTCGGGACTCGGACTCGGGTTCGGGTCG

P   E   E   D   G   S   P   D   P   E   P   S   P   E   P   E   P   K   P   S   -
```

Figure 1 – page 7

```
     CTTGAGCCCAACACCAGCCTGGAGCGTGAGCCCAGAC C AACTCCAGCCCCAGCCC AGC
301  ---------+---------+---------+---------+---------+---------+ 360
     GAACTCGGGTTGTGGTCGGACCTCGCACTCGGGTCTGGGTTGAGGTCGGGGTCGGGGTCG

L  E  P  N  T  S  L  E  R  E  P  R  P  N  S  S  P  S  P  S  -

CCC GGCCAGGCCTCTGAGACCCCGCACCCACGACCCTCA TAA TAAACACGTCGATTCTGT
361  ---------+---------+---------+---------+---------+---------+ 420
     GGGCCGGTCCGGAGACTCTGGGGCGTGGGTGCTGGGAGTATTATTTGTGCAGCTAAGACA

P  G  Q  A  S  E  T  P  H  P  R  P  S  *  (amino acid residues
                                                   262-350 of SEQ ID NO:16)

CCAGGTTCCTTGATGCGCTGTGGCAGGGCAGGCAGCGGGGCGTGGAGAATCCTCACCACA
421  ---------+---------+---------+---------+---------+---------+ 480
     GGTCCAAGGAACTACGCGACACCGTCCCGTCCGTCGCCCCGCACCTCTTAGGAGTGGTGT

CCAAGGCTTCCAGAGGCCGGGGTCCCCGACTCAGAATCCCGCCCAGAGGCAAAGGTGCTG
481  ---------+---------+---------+---------+---------+---------+ 540
     GGTTCCGAAGGTCTCCGGCCCCAGGGGCTGAGTCTTAGGGCGGGTCTCCGTTTCCACGAC

CAGGAACCCAGCGCTGGGCATCTCACTTCCCGGGGTGGGGGCCTGACTCCCCAGTCTGAG
541  ---------+---------+---------+---------+---------+---------+ 600
     GTCCTTGGGTCGCGACCCGTAGAGTGAAGGGCCCCACCCCCGGACTGAGGGGTCAGACTC

GGAGGAGGGGGCTGGGGGCCTGGACTCCTGGGTCTGAGGGAAGAGGGGCTGGGAGTCTGG
601  ---------+---------+---------+---------+---------+---------+ 660
     CCTCCTCCCCCGACCCCCGGACCTGAGGACCCAGACTCCCTTCTCCCCGACCCTCAGACC

ACTGCCGGGTCTGAAGGAGGAGAAGGCTGGGGGTCTGGACTCCCGGGTTTGAAGAAGGAG
661  ---------+---------+---------+---------+---------+---------+ 720
     TGACGGCCCAGACTTCCTCCTCTTCCGACCCCCAGACCTGAGGGCCCAAACTTCTTCCTC

GGGCTGGGA    (SEQ ID NO:13)
721  ---------  729
     CCCGACCCT    (SEQ ID NO:14)
```

Figure 3A

```
      CCGTGATCTCGGCTCACTGCAACCTCCGCCTCCTGGGTTCAAGCGATTCTCCTGCCTCAG
   1  ---------+---------+---------+---------+---------+---------+  60

CCTCCGGAGTAACTGGGAGTACAGGCATGCGCCACCACGCTTGGCTGATTTTTGTCTTTT
  61  ---------+---------+---------+---------+---------+---------+ 120

TAGTAGGGGCGGGGTTTCACCATGTTGGCCAGGCTGGTCTCAAACTCCTGACCTCAGGTG
 121  ---------+---------+---------+---------+---------+---------+ 180

ATCCACCCACCTCTGTCTCCCAAAGTGCTGGGATTACAGGAGTGTGCCACTGCGCCTGAC
 181  ---------+---------+---------+---------+---------+---------+ 240

CAGCTTTATAAAGTTTATAGGGACAGTGTCACCACTTTACAGAAGAGGGACTGAGGCTCT
 241  ---------+---------+---------+---------+---------+---------+ 300

GAGGAGGAAGTTCCTTGCCAGGGTCCGAGTGTCGCCACCCTGAGAACTCCAGCACCCACC
 301  ---------+---------+---------+---------+---------+---------+ 360

TCCCTACTCTCCCTCATGGCGTCTCCCCCACCTTTCCACAGCCAGAAGTTGCCAGGTGAA
 361  ---------+---------+---------+---------+---------+---------+ 420

TACTTCCGGTACAAGGGCGTCCCCTTCCCCGTCGGCCTGTACTCGCTCGAGAGCATCAGC
 421  ---------+---------+---------+---------+---------+---------+ 480

TTGGCGGAGAACACCCAAGATGTGCGGGACGACGACATCTTTATCATCACCTACCCCAAG
 481  ---------+---------+---------+---------+---------+---------+ 540

TCAGGCACGACCTGGATGATCGAGATCATCTGCTTAATCCTGAAGGAAGGGGATCCATCC
 541  ---------+---------+---------+---------+---------+---------+ 600

TGGATCCGCTCCGTGCCCATCTGGGAGCGGGCACCCTGGTGTGAGACCATTGTGGGTGCT
 601  ---------+---------+---------+---------+---------+---------+ 660

TTCAGCCTCCCGGACCAGTACAGCCCCCGCCTCATGAGCTCCCATCTTCCCATCCAGATC
 661  ---------+---------+---------+---------+---------+---------+ 720

TTCACCAAGGCCTTCTTCAGCTCCAAGGCCAAGGTGATCTACATGGGCCGCAACCCCCGG
 721  ---------+---------+---------+---------+---------+---------+ 780

GACGTTGTGGTCTCCCTCTATCATTACTCCAAGATCGCCGGGCAGTTAAAGGACCCGGGC
 781  ---------+---------+---------+---------+---------+---------+ 840

ACACCCGACCAGTTCCTGAGGGACTTCCTCAAAGGCGAAGTGCAGTTTGGCTCCTGGTTC
 841  ---------+---------+---------+---------+---------+---------+ 900

GACCACATTAAGGGCTGGCTTCGGATGAAGGGCAAAGACAACTTCCTATTTATCACCTAC
 901  ---------+---------+---------+---------+---------+---------+ 960

GAGGAGCTGCAGCAGGACTTACAGGGCTCCGTGGAGCGCATCTGTGGGTTCCTGGGCGT
 961  ---------+---------+---------+---------+---------+---------+ 1020

CCGCTGGGCAAGGAGGCACTGGGCTCCGTCGTGGCACACTCAACCTTCAGCGCCATGAAG
1021  ---------+---------+---------+---------+---------+---------+ 1080
```

Figure 3A – page 2

```
         GCCAACACCATGTCCAACTACACGCTGCTGCCTCCCAGCCTGCTGGACCACCGTCGCGGG
1081     ---------+---------+---------+---------+---------+---------+ 1140

GCCTTCCTCCGGAAAGGGGTCTGCGGCGACTGGAAGAACCACTTCACGGTGGCCCAGAGC
1141     ---------+---------+---------+---------+---------+---------+ 1200

GAAGCCTTCGATCGTGCCTACCGCAAGCAGATGCGGGGGATGCCGACCTTCCCCTGGGAT
1201     ---------+---------+---------+---------+---------+---------+ 1260

GAAGACCCGGAGGAGGATGGCAGCCCAGATCCTGAGCCCAGCCCTGAGCCTGAGCCCAAG
1261     ---------+---------+---------+---------+---------+---------+ 1320

CCCAGCCTTGAGCCCAACACCAGCCTGGAGCGTGAGCCCAGAC CAACTCCAGCCCCAAC
1321     ---------+---------+---------+---------+---------+---------+ 1380

CCC AGCCCC GGCCAGGCCTCTGAGACCCCGCACCCACGACCCTCATAATAAACACGTCGA
1381     ---------+---------+---------+---------+---------+---------+ 1440

TTCTGTCTAAAAAAAAAAAAAAAAAAAAAAAAAAAAAA    (SEQ ID NO:15)
1441     ---------+---------+---------+------- 1477
```

Figure 3B

```
Met-Ala-Ser-Pro-Pro-Pro-Phe-His-Ser-Gln-Lys-Leu-Pro-Gly-Glu-Tyr-   16
Phe-Arg-Tyr-Lys-Gly-Val-Pro-Phe-Pro-Val-Gly-Leu-Tyr-Ser-Leu-Glu-   32
Ser-Ile-Ser-Leu-Ala-Glu-Asn-Thr-Gln-Asp-Val-Arg-Asp-Asp-Asp-Ile-   48
Phe-Ile-Ile-Thr-Tyr-Pro-Lys-Ser-Gly-Thr-Thr-Trp-Met-Ile-Glu-Ile-   64
Ile-Cys-Leu-Ile-Leu-Lys-Glu-Gly-Asp-Pro-Ser-Trp-Ile-Arg-Ser-Val-   80
Pro-Ile-Trp-Glu-Arg-Ala-Pro-Trp-Cys-Glu-Thr-Ile-Val-Gly-Ala-Phe-   96
Ser-Leu-Pro-Asp-Gln-Tyr-Ser-Pro-Arg-Leu-Met-Ser-Ser-His-Leu-Pro-  112
Ile-Gln-Ile-Phe-Thr-Lys-Ala-Phe-Phe-Ser-Ser-Lys-Ala-Lys-Val-Ile-  128
Tyr-Met-Gly-Arg-Asn-Pro-Arg-Asp-Val-Val-Val-Ser-Leu-Tyr-His-Tyr-  144
Ser-Lys-Ile-Ala-Gly-Gln-Leu-Lys-Asp-Pro-Gly-Thr-Pro-Asp-Gln-Phe-  160
Leu-Arg-Asp-Phe-Leu-Lys-Gly-Glu-Val-Gln-Phe-Gly-Ser-Trp-Phe-Asp-  176
His-Ile-Lys-Gly-Trp-Leu-Arg-Met-Lys-Gly-Lys-Asp-Asn-Phe-Leu-Phe-  192
Ile-Thr-Tyr-Glu-Glu-Leu-Gln-Gln-Asp-Leu-Gln-Gly-Ser-Val-Glu-Arg-  208
Ile-Cys-Gly-Phe-Leu-Gly-Arg-Pro-Leu-Gly-Lys-Glu-Ala-Leu-Gly-Ser-  224
Val-Val-Ala-His-Ser-Thr-Phe-Ser-Ala-Met-Lys-Ala-Asn-Thr-Met-Ser-  240
Asn-Tyr-Thr-Leu-Leu-Pro-Pro-Ser-Leu-Leu-Asp-His-Arg-Arg-Gly-Ala-  256
Phe-Leu-Arg-Lys-Gly-Val-Cys-Gly-Asp-Trp-Lys-Asn-His-Phe-Thr-Val-  272
Ala-Gln-Ser-Glu-Ala-Phe-Asp-Arg-Ala-Tyr-Arg-Lys-Gln-Met-Arg-Gly-  288
Met-Pro-Thr-Phe-Pro-Trp-Asp-Glu-Asp-Pro-Glu-Glu-Asp-Gly-Ser-Pro-  304
Asp-Pro-Glu-Pro-Ser-Pro-Glu-Pro-Lys-Pro-Ser-Leu-Glu-Pro-  320
Asn-Thr-Ser-Leu-Glu-Arg-Glu-Pro-Arg-Pro-Asn-Ser-Ser-Pro-Asn-Pro-  336
Ser-Pro-Gly-Gln-Ala-Ser-Glu-Thr-Pro-His-Pro-Arg-Pro-Ser        350
```

(SEQ ID NO:16)

Figure 3C

```
       AGACGCTGTCGCTGCGCACACCTGGCCTCTGTGCCGCCTGCTCCCTGCTCGTCCTCCCCT
  1    ---------+---------+---------+---------+---------+---------+ 60

CCCCACCCTCACCCACCTGCCATGGACGGGCCCGCCGAGCCCCAGATCCCGGGCTTGTGG
 61    ---------+---------+---------+---------+---------+---------+ 120

GACACCTATGAAGATGACATCTCGGAAATCAGCCAGAAGTTGCCAGGTGAATACTTCCGG
121    ---------+---------+---------+---------+---------+---------+ 180

TACAAGGGCGTCCCCTTCCCCGTCGGCCTGTACTCGCTCGAGAGCATCAGCT[T]GGCGGAG
181    ---------+---------+---------+---------+---------+---------+ 240

AACACCCAAGATGTGCGGGACGACGACATCTTTATCATCACCTACCCCAAGTCAGGCACG
241    ---------+---------+---------+---------+---------+---------+ 300

ACCTGGATGATCGAGATCATCTGCTTAATCCTGAAGGAAGGGGATCCATCCTGGATCCGC
301    ---------+---------+---------+---------+---------+---------+ 360

TCCGTGCCCATCTGGGAGCGGGCACCCTGGTGTGAGACCATTGTGGGTGCCTTCAGCCTC
361    ---------+---------+---------+---------+---------+---------+ 420

CCGGACCAGTACAGCCCCCGCCTCATGAGCTCCATCTTCCCATCCAGATCTTCACCAAG
421    ---------+---------+---------+---------+---------+---------+ 480

GCCTTCTTCAGCTCCAAGGCCAAGGTGATCTACATGGGCCGCAACCCCCGGGACGTTGTG
481    ---------+---------+---------+---------+---------+---------+ 540

GTCTCCCTCTATCATTACTCCAAGATCGCCGGGCAGTTAAAGGACCCGGGCACACCCGAC
541    ---------+---------+---------+---------+---------+---------+ 600

CAGTTCCTGAGGGACTTCCTCAAAGGCGAAGTGCAGTTTGGCTCCTGGTTC[G]ACCACATT
601    ---------+---------+---------+---------+---------+---------+ 660

AAGGGCTGGCTTCGGATGAAGGGCAAAGACAACTTCCTATTTATCACCTACGAGGAGCTG
661    ---------+---------+---------+---------+---------+---------+ 720

CAGCAGGACTTACAGGGCTCCGTGGAGCGCATCTGTGGGTTCCTGGGCC[G]TCCGCTGGGC
721    ---------+---------+---------+---------+---------+---------+ 780

AAGGAGGCACTGGGCTCCGTCGTGGCACACTCAACCTTCAGCGCCATGAAGGCCAACACC
781    ---------+---------+---------+---------+---------+---------+ 840

ATGTCCAACTACACGCTGCTGCCTCCCAGCCTGCTGGACCACCGTCGCGGGGCCTTCCTC
841    ---------+---------+---------+---------+---------+---------+ 900

CGGAAAGGGGTCTGCGGCGACTGGAAGAACCACTTCACGGTGGCCCAGAGCGAAGCCTTC
901    ---------+---------+---------+---------+---------+---------+ 960

GATCGTGCCTACCGCAAGCAGATGCGGGGGATGCCGACCTTCCCCTGGGATGAAGACCCG
961    ---------+---------+---------+---------+---------+---------+ 1020

GAGGAGGATGGCAGCCCAGATCCTGAGCCCAGCCCTGAGCCTGAGCCCAAGCCCAGCCTT
1021   ---------+---------+---------+---------+---------+---------+ 1080
```

Figure 3C – page 2

```
        GAGCCCAACACCAGCCTGGAGCGTGAGCCCAGACCCAACTCCAGCCCCAGCCCCAGCCCC
1081    ---------+---------+---------+---------+---------+---------+ 1140

GGCCAGGCCTCTGAGACCCCGCACCCACGACCCTCATAATAAACACGTCGATTCTGTCTA
1141    ---------+---------+---------+---------+---------+---------+ 1200

AAAAAAAAAAAAAAAAAAAAAAAAAAAA    (SEQ ID NO:17)
1201    ---------+---------+-------- 1228
```

Figure 3D

```
Met-Asp-Gly-Pro-Ala-Glu-Pro-Gln-Ile-Pro-Gly-Leu-Trp-Asp-Thr-Tyr-   16
Glu-Asp-Asp-Ile-Ser-Glu-Ile-Ser-Gln-Lys-Leu-Pro-Gly-Glu-Tyr-Phe-   32
Arg-Tyr-Lys-Gly-Val-Pro-Phe-Pro-Val-Gly-Leu-Tyr-Ser-Leu-Glu-Ser-   48
Ile-Ser-Leu-Ala-Glu-Asn-Thr-Gln-Asp-Val-Arg-Asp-Asp-Asp-Ile-Phe-   64
Ile-Ile-Thr-Tyr-Pro-Lys-Ser-Gly-Thr-Thr-Trp-Met-Ile-Glu-Ile-Ile-   80
Cys-Leu-Ile-Leu-Lys-Glu-Gly-Asp-Pro-Ser-Trp-Ile-Arg-Ser-Val-Pro-   96
Ile-Trp-Glu-Arg-Ala-Pro-Trp-Cys-Glu-Thr-Ile-Val-Gly-Ala-Phe-Ser-  112
Leu-Pro-Asp-Gln-Tyr-Ser-Pro-Arg-Leu-Met-Ser-Ser-His-Leu-Pro-Ile-  128
Gln-Ile-Phe-Thr-Lys-Ala-Phe-Phe-Ser-Ser-Lys-Ala-Lys-Val-Ile-Tyr-  144
Met-Gly-Arg-Asn-Pro-Arg-Asp-Val-Val-Val-Ser-Leu-Tyr-His-Tyr-Ser-  160
Lys-Ile-Ala-Gly-Gln-Leu-Lys-Asp-Pro-Gly-Thr-Pro-Asp-Gln-Phe-Leu-  176
Arg-Asp-Phe-Leu-Lys-Gly-Glu-Val-Gln-Phe-Gly-Ser-Trp-Phe-Asp-His-  192
Ile-Lys-Gly-Trp-Leu-Arg-Met-Lys-Gly-Lys-Asp-Asn-Phe-Leu-Phe-Ile-  208
Thr-Tyr-Glu-Glu-Leu-Gln-Gln-Asp-Leu-Gln-Gly-Ser-Val-Glu-Arg-Ile-  224
Cys-Gly-Phe-Leu-Gly-Arg-Pro-Leu-Gly-Lys-Glu-Ala-Leu-Gly-Ser-Val-  240
Val-Ala-His-Ser-Thr-Phe-Ser-Ala-Met-Lys-Ala-Asn-Thr-Met-Ser-Asn-  256
Tyr-Thr-Leu-Leu-Pro-Pro-Ser-Leu-Leu-Asp-His-Arg-Arg-Gly-Ala-Phe-  272
Leu-Arg-Lys-Gly-Val-Cys-Gly-Asp-Trp-Lys-Asn-His-Phe-Thr—Val-Ala-  288
Gln-Ser-Glu-Ala-Phe-Asp-Arg-Ala-Tyr-Arg-Lys-Gln-Met-Arg-Gly-Met-  304
Pro-Thr-Phe-Pro-Trp-Asp-Glu-Asp-Pro-Glu-Glu-Asp-Gly-Ser-Pro-Asp-  320
Pro-Glu-Pro-Ser-Pro-Glu-Pro-Glu-Pro-Lys-Pro-Ser-Leu-Glu-Pro-Asn-  336
Thr-Ser-Leu-Glu-Arg-Glu-Pro-Arg-Pro-Asn-Ser-Ser-Pro-Ser-Pro-Ser-  352
Pro-Gly-Gln-Ala-Ser-Glu-Thr-Pro-His-Pro-Arg-Pro-Ser                365
```

(SEQ ID NO:18)

SEQUENCE LISTING

<160> NUMBER OF SEQ ID NOS: 34

<210> SEQ ID NO 1
<211> LENGTH: 969
<212> TYPE: DNA
<213> ORGANISM: Homo sapiens

<400> SEQUENCE: 1

```
gtctccgccc tccgtgtatc tctgttgcgt ctctcaaggt ctgtggcccc tgtgcatctc    60 agtccctcc tggtatctgt ctcccatgcc ctctgccctc tccctttctc cctggctccc   120
gccctgtctg tgctgccgtg gtcctggctg tgcctctgtc cctgtgtctg tttccagggt   180
gccccttacg cgtcagcccg tgagggcaag tttctgtctg cccttcccc agcggtggcc   240 tagtgcttgg aacagcgcct ggcagacagg agatgctcag taaatatttc tcaaatgaat   300
aaaggaatga atgagtgaat gaatgaatga atgaatgaac tcgctgagat gggcgagatc   360
agcgccattt cccaaatgag caacgtgggc tccaggtggg tgcccacagg cccagaactg   420
```

| | |
|---|---|
| ccagcccgga aggttctggc gtgggtttgg cactgacccc atggattctg ccccagctg | 480 |
| agcaccagac gccaggacgt gcccatcact gctcctcccc gccctcagaa cagggtggct | 540 |
| ccctctggcc tctccccgct gttggaggcg tgggtagcag ctgggagaac cggctgggtg | 600 |
| ctgcccctcc ccttgggccg gcacggagt aggcacctgg cgggctcccc aggtggcaga | 660 |
| cgctgtcgct gcgcacacct ggcctctgtg ccgcctgctc cctgctcgtc ctcccctccc | 720 |
| caccctcacc cacctgccat ggacgggccc gccgagcccc agatcccggg cttgtgggac | 780 |
| acctatgaag atgacatctc ggaaatcagg tgaggcccag acctgggcag gagccaggag | 840 |
| atcccaggga ggaggtggct gtttggggga gccggggact gtggcaaggg tggcctccag | 900 |
| ccacccgcag ccgcaggcct ggcccagact tagctggagg ggctgggctg ggctggggca | 960 |
| tccagtgtg | 969 |

<210> SEQ ID NO 2
<211> LENGTH: 969
<212> TYPE: DNA
<213> ORGANISM: Homo sapiens

<400> SEQUENCE: 2

| | |
|---|---|
| cacactggat gccccagccc agcccagccc ctccagctaa gtctgggcca ggcctgcggc | 60 |
| tgcgggtggc tggaggccac ccttgccaca gtccccggct cccccaaaca gccacctcct | 120 |
| ccctgggatc tcctggctcc tgcccaggtc tgggcctcac ctgatttccg agatgtcatc | 180 |
| ttcataggtg tcccacaagc ccgggatctg ggctcggcg ggcccgtcca tgcaggtgg | 240 |
| gtgagggtgg ggaggggagg acgagcaggg agcaggcggc acagaggcca ggtgtgcgca | 300 |
| gcgacacgcgt ctgccacctg gggagcccgc caggtgccta ctccgtgccc ggcccaaggg | 360 |
| gaggggcagc acccagccgg ttctcccagc tgctacccac gcctccaaca gcggggagag | 420 |
| gccagaggga gccaccctgt tctgaggcg gggaggagca gtgatgggca cgtcctggcg | 480 |
| tctggtgctc agctggggc agaatccatg gggtcagtgc caaacccacg ccagaacctt | 540 |
| ccgggctggc agttctgggc ctgtgggcac ccacctggag cccacgttgc tcatttggga | 600 |
| aatggcgctg atctcgccca tctcagcgag ttcattcatt cattcattca ttcactcatt | 660 |
| cattcctta ttcatttgag aaatatttac tgagcatctc ctgtctgcca ggcgctgttc | 720 |
| caagcactag gccaccgctg gggaaggggc agacagaaac ttgccctcac gggctgacgc | 780 |
| gtaaggggca ccctggaaac agacacaggg acagaggcac agccaggacc acggcagcac | 840 |
| agacagggcg ggagccaggg agaaagggag agggcagagg gcatgggaga cagataccag | 900 |
| gaggggactg agatgcacag gggccacaga ccttgagaga cgcaacagag atacacggag | 960 |
| ggcggagac | 969 |

<210> SEQ ID NO 3
<211> LENGTH: 819
<212> TYPE: DNA
<213> ORGANISM: Homo sapiens

<400> SEQUENCE: 3

| | |
|---|---|
| aggatgagag ccaggttcat tgaattccaa agaggctggg aaagaagagg gtgtattaac | 60 |
| tgagcacttg ctgtgtgcca ggattcatgc tcagtgcttg cttgctttta tttttttgag | 120 |
| acggagtctc tcactctgtc acccaggctg gagtgcagtg gcgtgatctc agctcactgc | 180 |
| agcttctgct tccagcttc aagcgattct cgtaactcag cctcccgagt ggctgggact | 240 |
| gcaggcgcat gcaaccacat ctggctaatt tttgtctttt tagtagagac agggtttcac | 300 |

-continued

| | |
|---|---:|
| catgttggcc aggctggtct caaactcctg acctcaggtg atccaccac ctctgtctcc | 360 |
| caaagtgctg ggattacagg agtgtgccac tgcgcctgac cagctttata aagtttatag | 420 |
| ggacagtgtc accactttac agaagaggga ctgaggctct gaggaggaag ttccttgcca | 480 |
| gggtccgagt gtcgccaccc tgagaactcc agcacccacc tccctactct ccctcatggc | 540 |
| gtctccccca cctttccaca gccagaagtt gccaggtgaa tacttccggt acaagggcgt | 600 |
| cccctccc gtcggcctgt actcgctcga gagcatcagc ttggcggaga cacccaaga | 660 |
| tgtgcgggac gacgacatct ttatcatcac ctaccccaag tcaggtacct gccgggctgc | 720 |
| gggcgtcggg ggctggggag agtggggagg gggtgcggca gaggacagga aaggcacata | 780 |
| gagaaggagg ggaggaggaa aagtggggcc gggtctgtt | 819 |

<210> SEQ ID NO 4
<211> LENGTH: 819
<212> TYPE: DNA
<213> ORGANISM: Homo sapiens

<400> SEQUENCE: 4

| | |
|---|---:|
| aacagacccg gccccacttt tcctcctccc ctccttctct atgtgccttt cctgtcctct | 60 |
| gccgcacccc ctccccactc tccccagccc ccgacgcccg cagcccggca ggtacctgac | 120 |
| ttggggtagg tgatgataaa gatgtcgtcg tcccgcacat cttgggtgtt ctccgccaag | 180 |
| ctgatgctct cgagcgagta caggccgacg gggaagggga cgcccttgta ccggaagtat | 240 |
| tcacctggca acttctggct gtggaaaggt ggggagacg ccatgaggga gagtagggag | 300 |
| gtgggtgctg gagttctcag ggtggcgaca ctcggaccct ggcaaggaac ttcctcctca | 360 |
| gagcctcagt ccctcttctg taaagtggtg acactgtccc tataaacttt ataaagctgg | 420 |
| tcaggcgcag tggcacactc ctgtaatccc agcactttgg gagacagagg tgggtggatc | 480 |
| acctgaggtc aggagtttga ccagcctg gccaacatgg tgaaaccctg tctctactaa | 540 |
| aaagacaaaa attagccaga tgtggttgca tgcgcctgca gtcccagcca ctcgggaggc | 600 |
| tgagttacga gaatcgcttg aagctgggaa gcagaagctg cagtgagctg agatcacgcc | 660 |
| actgcactcc agcctgggtg acagagtgag agactccgtc tcaaaaaaat aaaagcaagc | 720 |
| aagcactgag catgaatcct ggcacacagc aagtgctcag ttaatacacc ctcttctttc | 780 |
| ccagcctctt tggaattcaa tgaacctggc tctcatcct | 819 |

<210> SEQ ID NO 5
<211> LENGTH: 534
<212> TYPE: DNA
<213> ORGANISM: Homo sapiens

<400> SEQUENCE: 5

| | |
|---|---:|
| agcctgggcg acagagtaag actctgtctt aaaaaaaata ataaaaggtg gcaaattgct | 60 |
| caataagtgc tgttgtgatt attctgatga tatctccctc ttcagccctc ccacacccaa | 120 |
| ttaatctgct cgtttctccc aacaggcacg acctggatga tcgagatcat ctgcttaatc | 180 |
| ctgaaggaag gggatccatc ctggatccgc tccgtgccca tctgggagcg ggcaccctgg | 240 |
| tgtgagacca ttgtgggtgc cttcagcctc ccggaccagt acagccccg cctcatgagc | 300 |
| tcccatcttc ccatccagat cttcaccaag gccttcttca gctccaaggc caaggttggg | 360 |
| aggaggggtg tgtgtcagtt gggagggggct gcatgggtgt atggggtaat ggggggacgg | 420 |
| agcataactc attgattcat tcagcaccta tttgttaaac acttactatg tgcctgactc | 480 |
| tgatctagca cagtggtcaa tatacacaca gaaatgcctg ccctttggca ggga | 534 |

<210> SEQ ID NO 6
<211> LENGTH: 534
<212> TYPE: DNA
<213> ORGANISM: Homo sapiens

<400> SEQUENCE: 6

```
tccctgccaa agggcaggca tttctgtgtg tatattgacc actgtgctag atcagagtca      60
ggcacatagt aagtgtttaa caaataggtg ctgaatgaat caatgagtta tgctccgtcc     120
ccccattacc ccatacaccc atgcagcccc tcccaactga cacacacccc tcctcccaac     180
cttggccttg gagctgaaga aggccttggt gaagatctgg atgggaagat gggagctcat     240
gaggcggggg ctgtactggt ccgggaggct gaaggcaccc acaatggtct cacaccaggg     300
tgcccgctcc cagatgggca cggagcggat ccaggatgga tccccttcct tcaggattaa     360
gcagatgatc tcgatcatcc aggtcgtgcc tgttgggaga acgagcaga ttaattgggt      420
gtgggagggc tgaagaggga gatatcatca gaataatcac aacagcactt attgagcaat     480
ttgccacctt ttattatttt ttttaagaca gagtcttact ctgtcgccca ggct           534
```

<210> SEQ ID NO 7
<211> LENGTH: 378
<212> TYPE: DNA
<213> ORGANISM: Homo sapiens

<400> SEQUENCE: 7

```
aggggtctcc agggcaggag gcctcagggg ctggggtctt gcctgtgtct gacgccttct      60
cccctctcct caccatccgc acacaggtga tctacatggg ccgcaacccc cgggacgttg     120
tggtctccct ctatcattac tccaagatcg ccgggcagtt aaaggacccg gcacacccg      180
accagttcct gagggacttc ctcaaaggcg aaggtgggga cagggtaaag cggggcagga     240
ggggtgggga ggagccccag aggaccctga tgggcagagg acagaggag gggtaagaaa      300
gggagagaga cagagacaca gggcatcaaa aggggcaata gagacagaga gcaggtggcc     360
aggagaagaa gagacgga                                                   378
```

<210> SEQ ID NO 8
<211> LENGTH: 378
<212> TYPE: DNA
<213> ORGANISM: Homo sapiens

<400> SEQUENCE: 8

```
tccgtctctt cttctcctgg ccacctgctc tctgtctcta ttgccccttt tgatgccctg      60
tgtctctgtc tctctccctt tcttacccct cctctgtccc tctgcccatc agggtcctct     120
ggggctcctc cccaccccte ctgccccgct ttacctgtc cccaccttcg cctttgagga     180
agtccctcag gaactggtcg ggtgtgcccg ggtcctttaa ctgcccggcg atcttggagt     240
aatgatagag ggagaccaca acgtcccggg ggttgcggcc catgtagatc acctgtgtgc     300
ggatggtgag gagaggggag aaggcgtcag acacaggcaa gaccccagcc cctgaggcct     360
cctgccctgg agacccct                                                   378
```

<210> SEQ ID NO 9
<211> LENGTH: 336
<212> TYPE: DNA
<213> ORGANISM: Homo sapiens

```
<400> SEQUENCE: 9
cccagtgggg ctgggggaac ccgccactca gccctcaccc cacttgtccc tctgcccaca      60
gtgcagtttg gctcctggtt cgaccacatt aagggctggc ttcggatgaa gggcaaagac     120
aacttcctat ttatcaccta cgaggagctg cagcaggtga gtccccacct cctccaggtg     180
cagcgtcccc cccatacctt ctgctcacac cccacactct cccttcccg agggtctcag      240 gaccctccg cttccccatg caatgcgcca gccctgggg atactgcagg aacagaacag       300
aggccctgag cctgtgagca agaccacaga caaaat                               336

<210> SEQ ID NO 10
<211> LENGTH: 336
<212> TYPE: DNA
<213> ORGANISM: Homo sapiens

<400> SEQUENCE: 10
attttgtctg tggtcttgct cacaggctca gggcctctgt tctgttcctg cagtatcccc     60
aggggctggc gcattgcatg gggaagcgga agggtcctga accctcgggg aaggggagag    120 tgtgggtgt gagcagaagg tatggggggg acgctgcacc tggaggaggt ggggactcac     180
ctgctgcagc tcctcgtagg tgataaatag gaagttgtct ttgcccttca tccgaagcca    240
gcccttaatg tggtcgaacc aggagccaaa ctgcactgtg gcagaggga caagtggggt     300 gagggctgag tggcgggttc ccccagcccc actggg                              336

<210> SEQ ID NO 11
<211> LENGTH: 405
<212> TYPE: DNA
<213> ORGANISM: Homo sapiens

<400> SEQUENCE: 11
ctcaggcagc cccaggttag gacccagaca tgcggatccc aggttccacg ctccttcctt     60
ggccgagtgc cctccctccg ctggcccctc tcccctgcct gcaggactta cagggctccg    120
tggagcgcat ctgtgggttc ctgggccgtc cgctgggcaa ggaggcactg ggctccgtcg    180
tggcacactc aaccttcagc gccatgaagg ccaacaccat gtccaactac acgctgctgc    240
ctcccagcct gctggaccac cgtcgcgggg ccttcctccg gaaaggtgcg ggggttctgg    300
ggttcagagc ccactaggcc actgcccggc tgtgtgacct gggagagtta cttaacctct    360
ctgggcctca gtttctcacc cagctgtaac attgggtgaa caggg                    405

<210> SEQ ID NO 12
<211> LENGTH: 405
<212> TYPE: DNA
<213> ORGANISM: Homo sapiens

<400> SEQUENCE: 12
ccctgttcac ccaatgttac agctgggtga gaaactgagg cccagagagg ttaagtaact     60
ctcccaggtc acacagccgg gcagtggcct agtgggctct gaaccccaga accccgcac     120 ctttccggag gaaggccccg cgacggtggt ccagcaggct gggaggcagc agcgtgtagt    180
tggacatggt gttggccttc atggcgctga aggttgagtg tgccacgacg gagcccagtg    240
cctccttgcc cagcggacgg cccaggaacc cacagatgcg ctccacggag ccctgtaagt    300
cctgcaggca ggggagaggg gccagcggag ggagggcact cggccaagga aggagcgtgg    360
aacctgggat ccgcatgtct gggtcctaac ctggggctgc ctgag                    405
```

<210> SEQ ID NO 13
<211> LENGTH: 729
<212> TYPE: DNA
<213> ORGANISM: Homo sapiens

<400> SEQUENCE: 13

| | | | | | |
|---|---|---|---|---|---|
| ggacggtgtt | tctggcaaag | ggaacacctc | gccaaaggcc | gggaagggga | aggaggttgc | 60 |
| tggaatgttg | gaggtagggg | cgcagtgctc | cccagaggct | cctcacccc | tggtgcccc | 120 |
| tcttctccag | gggtctgtgg | cgactggaag | aaccacttca | cggtggccca | gagcgaagcc | 180 |
| ttcgatcgtg | cctaccgcaa | gcagatgcgg | gggatgccga | ccttccctg | ggatgaagac | 240 |
| ccggaggagg | acggcagccc | agatcctgag | cccagccctg | agcctgagcc | caagcccagc | 300 |
| cttgagccca | caccagcct | ggagcgtgag | cccagaccca | actccagccc | cagccccagc | 360 |
| cccggccagg | cctctgagac | cccgcaccca | cgaccctcat | aataaacacg | tcgattctgt | 420 |
| ccaggttcct | tgatgcgctg | tggcagggca | ggcagcgggg | cgtggagaat | cctcaccaca | 480 |
| ccaaggcttc | cagaggccgg | ggtccccgac | tcagaatccc | gcccagaggc | aaaggtgctg | 540 |
| caggaaccca | gcgctgggca | tctcacttcc | cggggtgggg | gcctgactcc | ccagtctgag | 600 |
| ggaggagggg | gctgggggcc | tggactcctg | ggtctgaggg | aagaggggct | gggagtctgg | 660 |
| actgccgggt | ctgaaggagg | agaaggctgg | gggtctggac | tcccgggttt | gaagaaggag | 720 |
| gggctggga | | | | | | 729 |

<210> SEQ ID NO 14
<211> LENGTH: 729
<212> TYPE: DNA
<213> ORGANISM: Homo sapiens

<400> SEQUENCE: 14

| | | | | | |
|---|---|---|---|---|---|
| tcccagcccc | tccttcttca | aacccgggag | tccagacccc | cagccttctc | ctccttcaga | 60 |
| cccggcagtc | cagactccca | gcccctcttc | cctcagaccc | aggagtccag | gcccccagcc | 120 |
| ccctcctccc | tcagactggg | gagtcaggcc | cccacccgg | gaagtgagat | gcccagcgct | 180 |
| gggttcctgc | agcacctttg | cctctgggcg | ggattctgag | tcggggaccc | cggcctctgg | 240 |
| aagccttggt | gtggtgagga | ttctccacgc | cccgctgcct | gccctgccac | agcgcatcaa | 300 |
| ggaacctgga | cagaatcgac | gtgtttatta | tgagggtcgt | gggtgcgggg | tctcagaggc | 360 |
| ctggccgggg | ctggggctgg | ggctggagtt | gggtctgggc | tcacgctcca | ggctggtgtt | 420 |
| gggctcaagg | ctgggcttgg | gctcaggctc | agggctgggc | tcaggatctg | gctgccgtc | 480 |
| ctcctccggg | tcttcatccc | agggaaggt | cggcatcccc | cgcatctgct | tgcggtaggc | 540 |
| acgatcgaag | gcttcgctct | gggccaccgt | gaagtggttc | ttccagtcgc | cacagacccc | 600 |
| tggagaagag | ggggcaccag | ggggtgagga | gcctctgggg | agcactgcgc | ccctacctcc | 660 |
| aacattccag | caacctcctt | ccccttcccg | gcctttggcg | aggtgttccc | tttgccagaa | 720 |
| acaccgtcc | | | | | | 729 |

<210> SEQ ID NO 15
<211> LENGTH: 1477
<212> TYPE: DNA
<213> ORGANISM: Homo sapiens

<400> SEQUENCE: 15

| | | | | | |
|---|---|---|---|---|---|
| ccgtgatctc | ggctcactgc | aacctccgcc | tcctgggttc | aagcgattct | cctgcctcag | 60 |
| cctccggagt | aactgggagt | acaggcatgc | gccaccacgc | ttggctgatt | tttgtctttt | 120 |

-continued

```
tagtaggggc ggggtttcac catgttggcc aggctggtct caaactcctg acctcaggtg    180
atccacccac ctctgtctcc caaagtgctg ggattacagg agtgtgccac tgcgcctgac    240
cagctttata agtttatag ggacagtgtc accactttac agaagaggga ctgaggctct     300
gaggaggaag ttccttgcca gggtccgagt gtcgccaccc tgagaactcc agcacccacc    360
tccctactct ccctcatggc gtctccccca cctttccaca gccagaagtt gccaggtgaa    420
tacttccggt acaagggcgt cccttccc gtcggcctgt actcgctcga gagcatcagc      480
ttggcggaga cacccaaga tgtgcgggac gacgacatct ttatcatcac ctaccccaag     540
tcaggcacga cctggatgat cgagatcatc tgcttaatcc tgaaggaagg ggatccatcc    600
tggatccgct ccgtgcccat ctgggagcgg gcaccctggt gtgagaccat tgtgggtgct    660
ttcagcctcc cggaccagta cagccccgc ctcatgagct cccatcttcc catccagatc     720
ttcaccaagg ccttcttcag ctccaaggcc aaggtgatct acatgggccg caaccccgg    780
gacgttgtgg tctccctcta tcattactcc aagatcgccg ggcagttaaa ggacccgggc    840
acacccgacc agttcctgag ggacttcctc aaaggcgaag tgcagtttgg ctcctggttc    900
gaccacatta agggctggct tcggatgaag ggcaaagaca acttcctatt tatcacctac    960
gaggagctgc agcaggactt acagggctcc gtggagcgca tctgtgggtt cctgggccgt   1020
ccgctgggca aggaggcact gggctccgtc gtggcacact caaccttcag cgccatgaag   1080
gccaacacca tgtccaacta cacgctgctg cctcccagcc tgctggacca ccgtcgcggg   1140
gccttcctcc ggaaaggggt ctgcggcgac tggaagaacc acttcacggt ggcccagagc   1200
gaagccttcg atcgtgccta ccgcaagcag atgcggggga tgccgacctt cccctgggat   1260
gaagacccgg aggaggatgg cagcccagat cctgagccca gccctgagcc tgagcccaag   1320
cccagccttg agcccaacac cagcctggag cgtgagccca gcccaactc cagccccaac    1380
cccagccccg gccaggcctc tgagacccg cacccacgac cctcataata aacacgtcga    1440
ttctgtctaa aaaaaaaaaa aaaaaaaaaa aaaaaaa                             1477
```

<210> SEQ ID NO 16
<211> LENGTH: 350
<212> TYPE: PRT
<213> ORGANISM: Homo sapiens

<400> SEQUENCE: 16

```
Met Ala Ser Pro Pro Phe His Ser Gln Lys Leu Pro Gly Glu Tyr
 1               5                  10                  15

Phe Arg Tyr Lys Gly Val Pro Phe Pro Val Gly Leu Tyr Ser Leu Glu
            20                  25                  30

Ser Ile Ser Leu Ala Glu Asn Thr Gln Asp Val Arg Asp Asp Asp Ile
        35                  40                  45

Phe Ile Ile Thr Tyr Pro Lys Ser Gly Thr Thr Trp Met Ile Glu Ile
    50                  55                  60

Ile Cys Leu Ile Leu Lys Glu Gly Asp Pro Ser Trp Ile Arg Ser Val
65                  70                  75                  80

Pro Ile Trp Glu Arg Ala Pro Trp Cys Glu Thr Ile Val Gly Ala Phe
                85                  90                  95

Ser Leu Pro Asp Gln Tyr Ser Pro Arg Leu Met Ser Ser His Leu Pro
            100                 105                 110

Ile Gln Ile Phe Thr Lys Ala Phe Phe Ser Ser Lys Ala Lys Val Ile
        115                 120                 125
```

```
Tyr Met Gly Arg Asn Pro Arg Asp Val Val Ser Leu Tyr His Tyr
    130                 135                 140

Ser Lys Ile Ala Gly Gln Leu Lys Asp Pro Gly Thr Pro Asp Gln Phe
145                 150                 155                 160

Leu Arg Asp Phe Leu Lys Gly Glu Val Gln Phe Gly Ser Trp Phe Asp
                165                 170                 175

His Ile Lys Gly Trp Leu Arg Met Lys Gly Lys Asp Asn Phe Leu Phe
            180                 185                 190

Ile Thr Tyr Glu Glu Leu Gln Gln Asp Leu Gln Gly Ser Val Glu Arg
            195                 200                 205

Ile Cys Gly Phe Leu Gly Arg Pro Leu Gly Lys Glu Ala Leu Gly Ser
        210                 215                 220

Val Val Ala His Ser Thr Phe Ser Ala Met Lys Ala Asn Thr Met Ser
225                 230                 235                 240

Asn Tyr Thr Leu Leu Pro Pro Ser Leu Leu Asp His Arg Arg Gly Ala
                245                 250                 255

Phe Leu Arg Lys Gly Val Cys Gly Asp Trp Lys Asn His Phe Thr Val
                260                 265                 270

Ala Gln Ser Glu Ala Phe Asp Arg Ala Tyr Arg Lys Gln Met Arg Gly
            275                 280                 285

Met Pro Thr Phe Pro Trp Asp Glu Asp Pro Glu Glu Asp Gly Ser Pro
    290                 295                 300

Asp Pro Glu Pro Ser Pro Glu Pro Lys Pro Ser Leu Glu Pro
305                 310                 315                 320

Asn Thr Ser Leu Glu Arg Glu Pro Arg Pro Asn Ser Ser Pro Asn Pro
                325                 330                 335

Ser Pro Gly Gln Ala Ser Glu Thr Pro His Pro Arg Pro Ser
            340                 345                 350

<210> SEQ ID NO 17
<211> LENGTH: 1228
<212> TYPE: DNA
<213> ORGANISM: Homo sapiens

<400> SEQUENCE: 17
agacgctgtc gctgcgcaca cctggcctct gtgccgcctg ctccctgctc gtcctcccct      60
ccccaccctc acccacctgc catggacggg cccgccgagc cccagatccc gggcttgtgg     120
gacacctatg aagatgacat ctcggaaatc agccagaagt tgccaggtga atacttccgg     180
tacaagggcg tccccttccc cgtcggcctg tactcgctcg agagcatcag cttggcggag     240
aacacccaag atgtgcggga cgacgacatc tttatcatca cctaccccaa gtcaggcacg     300
acctggatga tcgagatcat ctgcttaatc ctgaaggaag gggatccatc ctggatccgc     360
tccgtgccca tctgggagcg ggcaccctgg tgtgagacca ttgtgggtgc cttcagcctc     420
ccggaccagt acagccccg cctcatgagc tcccatcttc ccatccagat cttcaccaag     480
gccttcttca gctccaaggc caaggtgatc tacatgggcc gcaaccccg ggacgttgtg     540
gtctccctct atcattactc caagatcgcc gggcagttaa aggacccggg cacacccgac     600
cagttcctga gggacttcct caaaggcgaa gtgcagtttg gctcctggtt cgaccacatt     660
aagggctggc ttcggatgaa gggcaaagac aacttcctat ttatcaccta cgaggagctg     720
cagcaggact acagggctcg cgtggagcgc atctgtgggt tcctgggccg tccgctgggc     780
aaggaggcac tgggctccgt cgtggcacac tcaaccttca gcgccatgaa ggccaacacc     840
atgtccaact acacgctgct gcctcccagc ctgctggacc accgtcgcgg ggccttcctc     900
```

-continued

```
cggaaagggg tctgcggcga ctggaagaac cacttcacgg tggcccagag cgaagccttc    960
gatcgtgcct accgcaagca gatgcggggg atgccgacct tccctgggga tgaagacccg   1020
gaggaggatg gcagcccaga tcctgagccc agccctgagc ctgagcccaa gcccagcctt   1080
gagcccaaca ccagcctgga gcgtgagccc agacccaact ccagccccag ccccagcccc   1140
ggccaggcct ctgagacccc gcacccacga ccctcataat aaacacgtcg attctgtcta   1200
aaaaaaaaaa aaaaaaaaa aaaaaaaa                                        1228
```

<210> SEQ ID NO 18
<211> LENGTH: 365
<212> TYPE: PRT
<213> ORGANISM: Homo sapiens

<400> SEQUENCE: 18

```
Met Asp Gly Pro Ala Glu Pro Gln Ile Pro Gly Leu Trp Asp Thr Tyr
 1               5                  10                  15

Glu Asp Asp Ile Ser Glu Ile Ser Gln Lys Leu Pro Gly Glu Tyr Phe
            20                  25                  30

Arg Tyr Lys Gly Val Pro Phe Pro Val Gly Leu Tyr Ser Leu Glu Ser
        35                  40                  45

Ile Ser Leu Ala Glu Asn Thr Gln Asp Val Arg Asp Asp Ile Phe
    50                  55                  60

Ile Ile Thr Tyr Pro Lys Ser Gly Thr Thr Trp Met Ile Glu Ile Ile
65                  70                  75                  80

Cys Leu Ile Leu Lys Glu Gly Asp Pro Ser Trp Ile Arg Ser Val Pro
                85                  90                  95

Ile Trp Glu Arg Ala Pro Trp Cys Glu Thr Ile Val Gly Ala Phe Ser
            100                 105                 110

Leu Pro Asp Gln Tyr Ser Pro Arg Leu Met Ser Ser His Leu Pro Ile
        115                 120                 125

Gln Ile Phe Thr Lys Ala Phe Phe Ser Ser Lys Ala Lys Val Ile Tyr
    130                 135                 140

Met Gly Arg Asn Pro Arg Asp Val Val Ser Leu Tyr His Tyr Ser
145                 150                 155                 160

Lys Ile Ala Gly Gln Leu Lys Asp Pro Gly Thr Pro Asp Gln Phe Leu
                165                 170                 175

Arg Asp Phe Leu Lys Gly Glu Val Gln Phe Gly Ser Trp Phe Asp His
            180                 185                 190

Ile Lys Gly Trp Leu Arg Met Lys Gly Lys Asp Asn Phe Leu Phe Ile
        195                 200                 205

Thr Tyr Glu Glu Leu Gln Gln Asp Leu Gln Gly Ser Val Glu Arg Ile
    210                 215                 220

Cys Gly Phe Leu Gly Arg Pro Leu Gly Lys Glu Ala Leu Gly Ser Val
225                 230                 235                 240

Val Ala His Ser Thr Phe Ser Ala Met Lys Ala Asn Thr Met Ser Asn
                245                 250                 255

Tyr Thr Leu Leu Pro Pro Ser Leu Asp His Arg Arg Gly Ala Phe
            260                 265                 270

Leu Arg Lys Gly Val Cys Gly Asp Trp Lys Asn His Phe Thr Val Ala
        275                 280                 285

Gln Ser Glu Ala Phe Asp Arg Ala Tyr Arg Lys Gln Met Arg Gly Met
    290                 295                 300

Pro Thr Pro Trp Asp Glu Asp Pro Glu Glu Asp Gly Ser Pro Asp
305                 310                 315                 320
```

```
Pro Glu Pro Ser Pro Glu Pro Glu Lys Pro Ser Leu Glu Pro Asn
                325                 330                 335

Thr Ser Leu Glu Arg Glu Pro Arg Pro Asn Ser Ser Pro Ser Pro Ser
            340                 345                 350

Pro Gly Gln Ala Ser Glu Thr Pro His Pro Arg Pro Ser
        355                 360                 365

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
tgtaaaacga cggccagtag gatgagagcc aggttc                            36

<210> SEQ ID NO 20
<211> LENGTH: 37
<212> TYPE: DNA
<213> ORGANISM: Artificial Sequence
<220> FEATURE:
<223> OTHER INFORMATION: Primer

<400> SEQUENCE: 20
caggaaacag ctatgaccct gtaatcccag cactttg                           37

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
tgtaaaacga cggccagtgg gacagtgtca ccac                              34

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
caggaaacag ctatgaccct tctctatgtg cctttcc                           37

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
tgtaaaacga cggccagtag caccagacgc cagga                             35

<210> SEQ ID NO 24
<211> LENGTH: 35
<212> TYPE: DNA
<213> ORGANISM: Artificial Sequence
<220> FEATURE:
<223> OTHER INFORMATION: Primer
```

<400> SEQUENCE: 24
caggaaacag ctatgaccca cactggatgc cccag                                35

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
tgtaaaacga cggccagtgg tggcaaattg ctcaataa                             38

<210> SEQ ID NO 26
<211> LENGTH: 38
<212> TYPE: DNA
<213> ORGANISM: Artificial Sequence
<220> FEATURE:
<223> OTHER INFORMATION: Primer

<400> SEQUENCE: 26
caggaaacag ctatgaccat taccccatac acccatgc                             38

<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
tgtaaaacga cggccagtag gggtctccag ggca                                 34

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
caggaaacag ctatgacctc cgtctcttct ttctcctg                             38

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
tgtaaaacga cggccagtct caccccactt gtccct                               36

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
caggaaacag ctatgaccag cctgctgtgt ggt                                  33

```
-continued

<210> SEQ ID NO 31
<211> LENGTH: 35
<212> TYPE: DNA
<213> ORGANISM: Artificial Sequence
<220> FEATURE:
<223> OTHER INFORMATION: Primer

<400> SEQUENCE: 31
tgtaaaacga cggccagtgt taggacccag acatg                              35

<210> SEQ ID NO 32
<211> LENGTH: 37
<212> TYPE: DNA
<213> ORGANISM: Artificial Sequence
<220> FEATURE:
<223> OTHER INFORMATION: Primer

<400> SEQUENCE: 32
caggaaacag ctatgaccaa tgttacagct gggtgag                            37

<210> SEQ ID NO 33
<211> LENGTH: 34
<212> TYPE: DNA
<213> ORGANISM: Artificial Sequence
<220> FEATURE:
<223> OTHER INFORMATION: Primer

<400> SEQUENCE: 33
tgtaaaacga cggccagtgg acggtgtttc tggc                               34

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34
caggaaacag ctatgaccgg tgtggtgagg attct                              35
```

US 7,820,805 B2

SULFOTRANSFERASE 2B1 PHARMACOGENETICS

CROSS-REFERENCE TO RELATED APPLICATIONS

This application is a divisional of U.S. application Ser. No. 10/702,981, filed on Nov. 6, 2003 now U.S. Pat. No. 7,288,642, which claims benefit of U.S. Provisional Application No. 60/424,420, filed Nov. 7, 2002.

STATEMENT AS TO FEDERALLY SPONSORED RESEARCH

This invention was made with government support under grant number U01-GM61388, awarded by the National Institutes of Health. The federal government may have has certain rights in the invention.

TECHNICAL FIELD

This invention relates to sulfotransferase 2B1 nucleic acid and amino acid sequence variants.

BACKGROUND

Sulfate conjugation is an important pathway in the biotransformation of many neurotransmitters, hormones, drugs and other xenobioties, and is catalyzed by cytosolic sulfotransferase enzymes designated "SULT." SULT enzymes are encoded by a gene superfamily, which, in mammals, is divided into two families: SULT1, or phenol SULTs, and SULT2, or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) SULTs. SULT2 subfamilies include two hydroxysteroid SULTs, 2A1 and 2B1.

Members of the SULT2B subfamily, including SULT2B1, catalyze the sulfate conjugation of substrates such as DHEA, cholesterol, Minoxidil, pregnenolone, epiandrosterone, and andreostenediol. SULT2B1 is expressed in placenta, prostate, trachea, skin, liver, colon, small intestine, ovary, uterus, and fetal brain.

SUMMARY

The invention is based on the discovery of sequence variants that occur in both coding and non-coding regions of SULT2B1 nucleic acids. Certain SULT2B1 nucleotide sequence variants can be associated with individual differences in enzymatic activity of the encoded SULT2B1 enzymes. Other SULT2B1 nucleotide sequence variants in non-coding regions of the SULT2B1 nucleic acid may alter regulation of transcription and/or splicing of the SULT2B1 nucleic acid. Discovery of these sequence variants allows individual differences in the sulfate conjugation of hydroxysteroid molecules [(e.g., dehydroepiandrosterone (DHEA)] in humans to be assessed such that particular treatment regimens can be tailored to an individual based on the presence or absence of one or more sequence variants. Identification of SULT2B1 nucleotide sequence variants also allows predisposition to hydroxysteroid-dependent diseases to be assessed in individuals.

The invention features an isolated nucleic acid molecule containing a SULT2B1 nucleic acid sequence, wherein the nucleic acid molecule is at least ten nucleotides in length, and wherein the SULT2B1 nucleic acid sequence contains a nucleotide sequence variant relative to SEQ ID NO:1, SEQ ID NO:3, SEQ ID NO:5, SEQ ID NO:7, SEQ ID NO:9, SEQ ID NO:11, or SEQ ID NO:13. The nucleotide sequence variant can be at a position selected from the group consisting of: a) position −183, −21, 14, 75, 107, 525, 526, 555, 592, 644, 903, 989, or 1009 relative to the adenine of the SULT2B1 translation initiation codon; b) position 22 or 23 relative to the guanine in the splice donor site of intron 1a; c) position 88, 94, or 172 relative to the guanine in the splice donor site of intron 4; and d) position 3 relative to the guanine in the splice donor site of intron 5. The nucleotide sequence variant can be a nucleotide substitution.

The nucleotide sequence variant can be selected from the group consisting of a thymine substitution for cytosine at position 14 relative to the adenine of the SULT2B1 translation initiation codon, a thymine substitution for cytosine at position 75 relative to the adenine of the SULT2B1 translation initiation codon, and a cytosine substitution for thymine at position 107 relative to the adenine of the SULT2B1 translation initiation codon. The nucleotide sequence variant relative to the adenine of the SULT2B1 translation initiation codon can be selected from the group consisting of a thymine substitution for cytosine at position 525, an adenine substitution for guanine at position 526, an adenine substitution for guanine at position 555, and a thymine substitution for cytosine at position 592.

The isolated nucleic acid molecule of claim 1, wherein the nucleotide sequence variant relative to the adenine of the SULT2B1 translation initiation codon is selected from the group consisting of an adenine substitution for guanine at position 644 relative to the adenine of the SULT2B1 translation initiation codon, a thymine substitution for cytosine at position 903, and a thymine substitution for cytosine at position 989 relative to the adenine of the SULT2B1 translation initiation codon. The nucleotide sequence variant at position 22 or 23 relative to the guanine in the splice donor site of intron 1a can be a thymine substitution for cytosine at position 22 or an adenine substitution for guanine at position 23. The nucleotide sequence variant at position 88, 94, or 172 relative to the guanine in the splice donor site of intron 4 can be an adenine substitution for cytosine at position 88, an adenine substitution for guanine at position 94, or a guanine substitution for adenine at position 172. The nucleotide sequence variant at position 3 relative to the guanine in the splice donor site of intron 5 can be an adenine substitution for guanine. The nucleotide sequence variant at position −183 or −21 relative to the adenine of the SULT2B1 translation initiation codon can be a thymine substitution for cytosine at position −183 or a thymine substitution for cytosine at position −21.

In another aspect, the invention features an isolated nucleic acid encoding a SULT2B1 polypeptide, wherein the polypeptide contains a SULT2B1 amino acid sequence variant relative to the amino acid sequence of SEQ ID NO:15, and wherein the amino acid sequence variant is at a residue selected from the group consisting of 36, 176, 215, and 330. The invention also features an isolated nucleic acid encoding a SULT2B1 polypeptide, wherein the polypeptide contains a SULT2B1 amino acid sequence variant relative to the amino acid sequence of SEQ ID NO:17, and wherein the amino acid sequence variant is at a residue selected from the group consisting of 51, 191, 230, and 345.

In another aspect, the invention features an isolated SULT2B1 polypeptide, wherein the polypeptide contains a SULT2B1 amino acid sequence variant relative to the amino acid sequence of SEQ ID NO:15, and wherein the amino acid sequence variant is at a residue selected from the group consisting of 36, 176, 215, and 330. The amino acid sequence variant at residue 36 can be serine, the amino acid sequence variant at residue 176 can be asparagine, the amino acid sequence variant at residue 215 can be histidine, and the amino acid sequence variant at residue 330 can be leucine.

The invention also features an isolated SULT2B1 polypeptide, wherein the polypeptide contains a SULT2B1 amino acid sequence variant relative to the amino acid sequence of SEQ ID NO:17, and wherein the amino acid sequence variant is at a residue selected from the group consisting of 51, 191, 230, and 345. The amino acid sequence variant at residue 51 can be serine, the amino acid sequence variant at residue 191 can be asparagine, the amino acid sequence variant at residue 230 can be histidine, and the amino acid sequence variant at residue 345 can be leucine.

In yet another aspect, the invention features an article of manufacture containing a substrate, wherein the substrate contains a population of isolated SULT2B1 nucleic acid molecules of claim 1. The substrate can contain a plurality of discrete regions, wherein each region contains a different population of isolated SULT2B1 nucleic acid molecules, and wherein each population of molecules contains a different SULT2B1 nucleotide sequence variant.

In still another aspect, the invention features a method for determining if a mammal is predisposed to a dermal disease. The method can involve: a) obtaining a biological sample from the mammal, and b) detecting the presence or absence of a SULT2B1 nucleotide sequence variant in the sample, wherein predisposition to the dermal disease is determined based on the presence or absence of the variant. The method can further involve detecting the presence or absence of a plurality of the SULT2B1 nucleotide sequence variants in the sample to obtain a variant profile of the mammal, wherein predisposition to the dermal disease is determined based on the variant profile. The dermal disease can be ichythyosis.

The invention also features a method for assisting a medical or research professional. The method can involve: a) obtaining a biological sample from a mammal, and b) detecting the presence or absence of a plurality of SULT2B1 nucleotide sequence variants in the sample to obtain a variant profile of the mammal. The method can further involve communicating the profile to the medical or research professional.

In another aspect, the invention features an isolated nucleic acid molecule containing a SULT2B1 nucleic acid sequence, wherein the nucleic acid molecule is at least ten nucleotides in length, and wherein the SULT2B1 nucleic acid sequence has at least 99% sequence identity to a region of SEQ ID NO:15. Nucleotide 107 relative to the adenine of the SULT2B1 translation initiation codon can be a cytosine, nucleotide 526 relative to the adenine of the SULT2B1 translation initiation codon can be an adenine, nucleotide 644 relative to the adenine of the SULT2B1 translation initiation codon can be an adenine, or nucleotide 989 relative to the adenine of the SULT2B1 translation initiation codon can be a thymine. The region can be selected from the group consisting of: a) nucleotides 55 to 150 of SEQ ID NO:15 relative to the adenine of the SULT2B1 translation initiation codon; b) nucleotides 475 to 575 of SEQ ID NO:15 relative to the adenine of the SULT2B1 translation initiation codon; c) nucleotides 600 to 700 of SEQ ID NO:15 relative to the adenine of the SULT2B1 translation initiation codon; and d) nucleotides 950 to 1050 of SEQ ID NO:15 relative to the adenine of the SULT2B1 translation initiation codon.

In yet another aspect, the invention features an isolated nucleic acid molecule containing a SULT2B1 nucleic acid sequence, wherein the nucleic acid molecule is at least ten nucleotides in length, and wherein the SULT2B1 nucleic acid sequence has at least 99% sequence identity to a region of SEQ ID NO:17. Nucleotide 152 relative to the adenine of the SULT2B1 translation initiation codon can be a cytosine, nucleotide 571 relative to the adenine of the SULT2B1 translation initiation codon can be an adenine, nucleotide 689 relative to the adenine of the SULT2B1 translation initiation codon can be an adenine, or nucleotide 1034 relative to the adenine of the SULT2B1 translation initiation codon can be a thymine. The region can be selected from the group consisting of: a) nucleotides 115 to 200 of SEQ ID NO:17 relative to the adenine of the SULT2B1 translation initiation codon; b) nucleotides 530 to 630 of SEQ ID NO:17 relative to the adenine of the SULT2B1 translation initiation codon; c) nucleotides 600 to 700 of SEQ ID NO:17 relative to the adenine of the SULT2B1 translation initiation codon; and d) nucleotides 950 to 1050 of SEQ ID NO:17 relative to the adenine of the SULT2B1 translation initiation codon.

In another aspect, the invention features a method for determining the sulfonator status of an individual. The method can include determining whether the subject contains a variant SULT2B1 nucleic acid.

In still another aspect, the invention features a method for predicting the therapeutic efficacy of a compound in a subject, wherein metabolism of the compound includes sulfation. The method can include (a) determining the sulfonator status of the subject; and (b) correlating the sulfonator status with the ability of the subject to metabolize the compound, wherein the compound is predicted to be therapeutically effective if the sulfonator status is enhanced in the subject, and wherein the compound is predicted not to be therapeutically effective if the sulfonator status is reduced in the subject. Determination of the sulfonator status can include determining whether the subject contains a variant SULT2B1 nucleic acid. The variant SULT2B1 nucleic acid can contain a non-synonymous single nucleotide polymorphism. Alternatively, determination of the sulfonator status can include measuring sulfotransferase activity in a biological sample from the subject. The sulfotransferase activity can be SULT2B1 activity.

The invention also features a method for predicting the therapeutic efficacy of a compound in a subject, wherein metabolism of the compound includes sulfation. The method can include (a) estimating the level of sulfotransferase activity in the subject; and (b) correlating the level of sulfotransferase activity with the ability of the subject to metabolize the compound, wherein the compound is predicted to be therapeutically effective if the level of sulfotransferase activity is increased in the subject, and wherein the compound is predicted not to be therapeutically effective if the level of sulfotransferase activity is reduced in the subject. The sulfotransferase can be SULT2B1. The sulfotransferase activity can be estimated in vitro in a biological sample from the subject. The level of sulfotransferase activity in the subject can be estimated by determining whether the subject contains a variant SULT2B1 nucleic acid. The variant SULT2B1 nucleic acid can include a non-synonymous single nucleotide polymorphism.

In yet another aspect, the invention features a method for estimating the dose of a compound for administration to a subject, wherein metabolism of the compound includes sulfation. The method can include determining the level of sulfotransferase activity in a biological sample from the subject, wherein the dose is estimated to be higher if the level of sulfotransferase activity is increased in the biological sample as compared to a control level of sulfotransferase activity, and wherein the dose is estimated to be lower if the level of sulfotransferase activity is decreased in the biological sample as compared to the control level of sulfotransferase activity. The sulfotransferase activity can be SULT2B1 activity. Determination of the level of sulfotransferase activity can include determining whether the subject contains a variant SULT2B1 nucleic acid. The variant SULT2B1 nucleic acid can contain a non-synonymous single nucleotide polymorphism.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a depiction of the nucleotide sequence of the reference SULT2B1 (SEQ ID NOS:1 to 14), also showing the amino acid sequences encoded by the exons (portions of SEQ ID NO:16 and SEQ ID NO:18, as indicated). Exons are depicted in bold type and introns are in regular type. Positions of single nucleotide polymorphisms (SNPs) are boxed, as are the positions of amino acid changes that result from the SNPs. Primers are underlined, and start and stop codons are double-underlined.

FIG. 3A is a depiction of a nucleotide sequence (SEQ ID NO:15) containing the cDNA sequence of the reference SULT2B1a (nucleotides 376 to 1428). Start and stop codons are shown in bold text. Positions of SNPs are boxed. FIG. 3B is a depiction of the amino acid sequence (SEQ ID NO:16) of the reference SULT2B1a. FIG. 3C is a depiction of a nucleotide sequence (SEQ ID NO:17) containing the cDNA sequence of the reference SULT2B1b (nucleotides 82 to 1189). Start and stop codons are shown in bold text. Positions of SNPs are boxed. FIG. 3D is a depiction of the amino acid sequence (SEQ ID NO:18) of the reference SULT2B1b.

DETAILED DESCRIPTION

Figure 2:
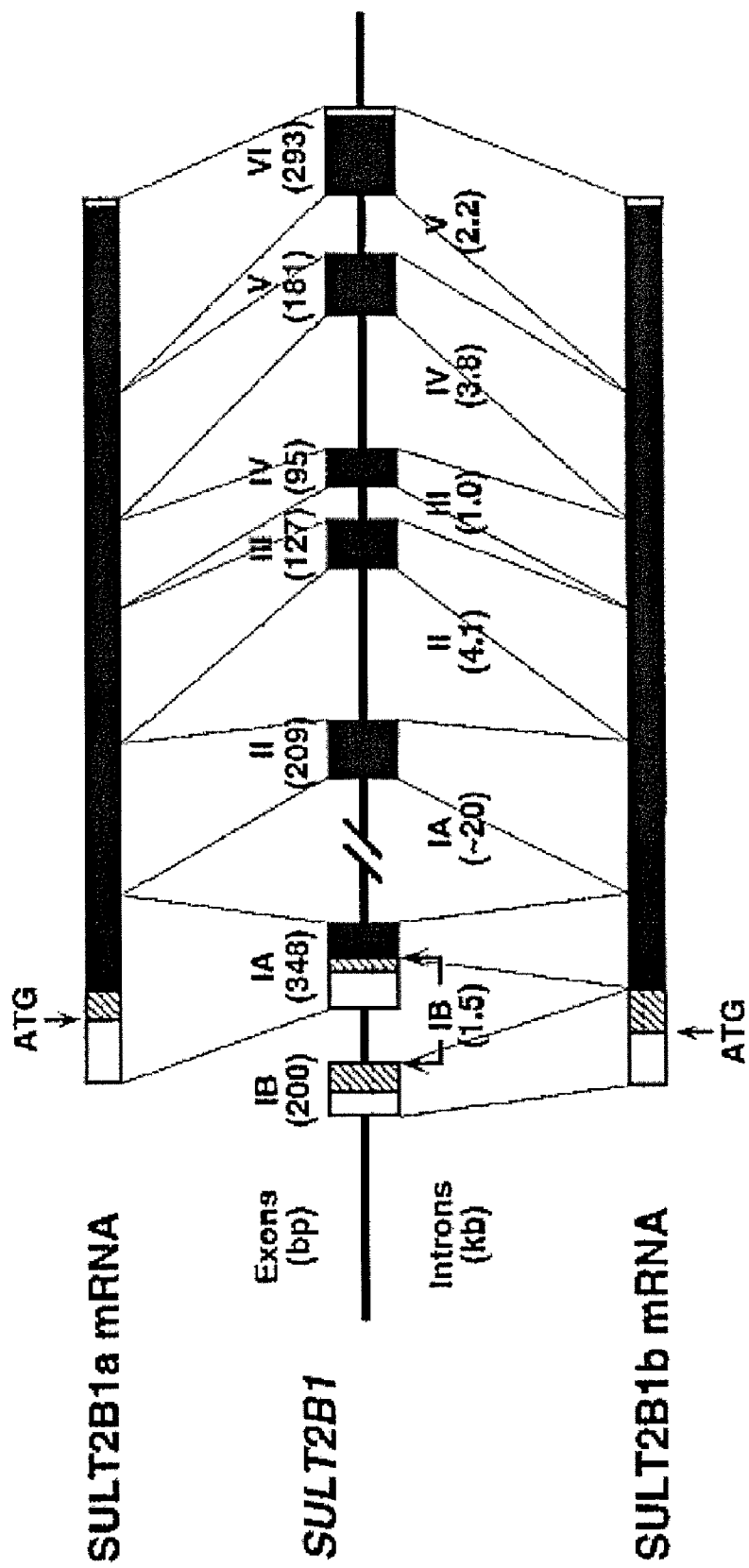
FIG. 2 is a diagram depicting the human SULT2B1 gene structure, as well as structures of the two mRNAs encoded by this gene. Black and cross-hatched rectangles represent portions of exons that encode mRNA ORF sequences. Open rectangles represent 5'- and 3' UTR-sequences. Exon lengths in base pairs and intron lengths in kilobases also are indicated.

The invention features SULT2B1 nucleotide and SULT2B1 amino acid sequence variants. SULT2B1 catalyzes the transfer of inorganic sulfate to hydroxysteroids such as DHEA, and uses 3'-phosphoadenosine-5'-phosphosulfate (PAPS) as the sulfate donor. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. SULT2B1 plays a role in the modification of molecules including DHEA, cholesterol, Minoxidil, pregnenolone, epiandrosterone, and androstenediol.

Genetically-based variations in SULT2B1 activity may affect the metabolism of molecules such as DHEA. In addition, variations in SULT2B1 can affect metabolism of estrogen-related hormones such as those found in contraceptives. Thus, detecting sulfotransferase nucleic acid and amino acid sequence variants may facilitate the prediction of therapeutic efficacy and toxicity of drugs on an individual basis. Detection of such variants also can indicate a predisposition to dermal diseases such as ichthyosis, in which there is a deficiency of cholesterol sulfate synthesis.

Nucleic Acid Molecules

The invention features isolated nucleic acids that include a SULT2B1 nucleic acid sequence. The SULT2B1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-SULT2B1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in sense or antisense orientation, can be complementary to the SULT2B1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in the SULT2B1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference SULT2B1 genomic nucleic acid sequence is provided in FIG. 1 (SEQ ID NOS:1 to 14) and in GenBank (Accession Nos. U92316, U92317, U92318, U92319, U92320, U92321, and U92322). Transcripts of the SULT2B1 gene are subject to alternative splicing, resulting in SULT2B1a and SULT2B1b mRNAs. FIG. 2 is a diagram showing the human SULT2B1 gene structure, as well as structures of the mRNAs encoded by the gene. The SULT2B1a and SULT2B1b mRNAs differ at their 5' termini, and have 1050- and 1095-base pair open reading frames that encode 350 and 365 amino acids, respectively. The SULT2B1a cDNA is encoded by exons 1A and 2-6. Exon 1A contains 179 nucleotides of 5'-UTR and the first 169 base pairs of the SULT2B1a coding sequence. The SULT2B1b cDNA is encoded by exon 1B, the final 143 nucleotides of exon 1A, and exons 2-6. Exon 1B contains the entire 5'-UTR and the first 71 base pairs of the SULT2B1b ORF. See, Her et al. (1998) *Genomics* 53:284-295.

Reference SULT2B1a and SULT2B1b nucleotide sequences, including the SULT2B1a and SULT2B1b cDNAs, are provided in FIGS. 3A and 3C (SEQ ID NOS:15 and 17, respectively) and the corresponding amino acid sequences are provided in FIGS. 3B and 3D (SEQ ID NOS:16 and 18, respectively). Both the mRNA and the amino acid sequences for SULT2B1a and SULT2B1b also can be found in GenBank (Accession Nos. U92314 and U92315, respectively).

The nucleic acid and amino acid reference sequences also are referred to herein as "wild type." As used herein, "untranslated sequence" includes 5' and 3' flanking regions that are outside of the mRNA as well as 5' and 3' untranslated regions (5'-UTR or 3'-UTR) that are part of the mRNA, but are not translated. Positions of nucleotide sequence variants in 5' untranslated sequences are designated as "−X" relative to the "A" in the initiation codon; positions of nucleotide sequence variants in the coding sequence and 3' untranslated sequence are designated as "+X" or "X" relative to the "A" in the initiation codon. Nucleotide sequence variants that occur in introns are designated as "+X" or "X" relative to "G" in the splice donor site (GT) or as "−X" relative to the "G" in the splice acceptor site (AG).

In some embodiments, a SULT2B1 nucleotide sequence variant encodes a SULT2B1 polypeptide having a SULT2B1 amino acid sequence variant. The term "polypeptide" refers to a chain of at least four amino acid residues (e.g., 4-8, 9-12, 13-15, 16-18, 19-21, 22-100, 100-150, 150-200, 200-300 residues, or a full-length SULT2B1 polypeptide). SULT2B1 polypeptides may or may not have sulfotransferase catalytic activity, or may have activity that is altered relative to the reference SULT2B1 polypeptide. Polypeptides that do not have activity or that have altered activity are useful for diagnostic purposes (e.g., for producing antibodies having specific binding affinity for variant sulfotransferase polypeptides).

Corresponding SULT2B1 polypeptides, irrespective of length, that differ in amino acid sequence are herein referred to as allozymes. For example, a SULT2B1a nucleic acid sequence that includes a cytosine at nucleotide 107 (nucleotide 152 of SULT2B1b) encodes a SULT2B1 polypeptide having a serine at amino acid residue 36 (amino acid residue 51 if translated from a SULT2B1b cDNA). This polypeptide (Leu36Ser) would be considered an allozyme with respect to the reference SULT2B1 polypeptide that contains a leucine at amino acid residue 36. Additional non-limiting examples of SULT2B1 nucleotide sequence variants that encode SULT2B1 amino acid sequence variants include variants at nucleotides 526, 644, 789, 989, or 1009. For example, a SULT2B1a nucleic acid molecule can include an adenine at nucleotide 526 (nucleotide 571 of SULT2B1b) and encode a SULT2B1 polypeptide having an asparagine residue at amino acid residue 176 (amino acid residue 191 if translated from a SULT2B1b cDNA) in place of an aspartate residue (Asp 176Asn); a SULT2B1a nucleic acid molecule can include an adenine at nucleotide 644 (nucleotide 689 of SULT2B1b) and encode a SULT2B1 polypeptide having a histidine residue at amino acid residue 215 (amino acid residue 230 if translated from a SULT2B1b cDNA) in place of an arginine residue (Arg215His); a SULT2B1a nucleic acid molecule can include a thymine at nucleotide 989 (nucleotide 1034 of SULT2B1b) and encode a SULT2B1 polypeptide having a leucine residue at amino acid residue 330 (amino acid residue 345 if translated from a SULT2B1b cDNA) in place of a proline residue (Pro330Leu); or a SULT2B1a nucleic acid molecule can include variants at nucleotides 1009-1014 (nucleotides 1054-1059 of SULT2B1b) and encode a SULT2B1 polypeptide having altered residues at amino acid residues 337 and 338 (amino acid residues 352 and 353 if translated from a SULT2B1b cDNA) in place of the serine and proline residues normally present.

SULT2B1 allozymes as described above are encoded by a series of sulfotransferase alleles. These alleles represent SULT2B1 nucleic acid sequences containing nucleotide sequence variants, typically multiple nucleotide sequence variants, within coding and non-coding sequences. Representative examples of single nucleotide sequence variants are described above. Table 2 includes SULT2B1 alleles that encode SULT2B1 amino acid sequence variants. Nucleotide positions are given with reference to the SULT2B1a sequence. Alleles encoding Leu36Ser are commonly observed in Caucasians (allele frequencies >1%), while alleles encoding Pro330Leu are commonly observed in both Caucasians and African Americans. The relatively large number of alleles and allozymes for SULT2B1 indicates the potential complexity of SULT pharmacogenetics. Such complexity emphasizes the need for determining single nucleotide sequence variants, (i.e., single nucleotide polymorphisms, SNPs) as well as complete SULT2B1 haplotypes (i.e., the set of alleles on one chromosome or a part of a chromosome) of patients.

Certain SULT2B1 nucleotide sequence variants do not alter the amino acid sequence. Such variants, however, could alter regulation of transcription as well as mRNA stability. SULT2B1 nucleotide sequence variants can occur in intron sequences, for example, within introns 1, 2, 3, 4, or 5. In particular, the nucleotide sequence variant can include a thymine at nucleotide 22 or a cytosine at nucleotide 23 of intron 1a. The nucleotide sequence variant can include a thymine at nucleotide −10 of intron 2. Intron 4 variants can include an adenine at nucleotide 88, an adenine at nucleotide 94, a guanine at nucleotide 172, or a thymine at nucleotide −41. Intron 5 variants include an adenine at nucleotide 3.

SULT2B1 nucleotide sequence variants that do not change the amino acid sequence also can be within an exon or in 5' or 3' untranslated sequences. For example, the 5' flanking region of SULT2B1b can include a thymine at position −21, and the 5' flanking region of SULT2B1a can include a thymine at position −183.

In some embodiments, nucleic acid molecules of the invention can have at least 98% (e.g., 98.5%, 99.0%, 99.5%, 99.6%, 99.7%, 99.8%, 99.9%, or 100%) sequence identity with a region of SEQ ID NO:15 or SEQ ID NO:17 that includes one or more variants described herein. The region of SEQ ID NO:15 is at least 15 nucleotides in length (e.g., 50, 60, 70, 75, 100, 150 or more nucleotides in length). For example, a nucleic acid molecule can have at least 99% identity with a region of SEQ ID NO:15 containing nucleotides −150 to 1400, −150 to −75, −75 to −30, −25 to 50, 55 to 150, 115 to 200, 205 to 275, 300 to 375, 380 to 450, 455 to 525, 475 to 575, 530 to 630, 600 to 700, 650 to 700, 705 to 745, 750 to 800, 805 to 900, 950 to 1050, 1075 to 1175, 1200 to 1300, or 1300 to 1400 relative to the adenine of the SULT2B1 translation initiation codon, where the nucleotide sequence of SEQ ID NO:15 includes one or more of the variants described herein. For example, the nucleotide sequence of SEQ ID NO:15 can have a cytosine at nucleotide 107 relative to the adenine of the SULT2B1 translation initiation codon, an adenine at nucleotide 526 relative to the adenine of the SULT2B1 translation initiation codon, an adenine at nucleotide 644 relative to the adenine of the SULT2B1 translation initiation codon, or a thymine at nucleotide 989 relative to the adenine of the SULT2B1 translation initiation codon, and combinations thereof. In another embodiment, the nucleotide sequence of SEQ ID NO:17 can have a cytosine at nucleotide 152 relative to the adenine of the SULT2B1 translation initiation codon, an adenine at nucleotide 571 relative to the adenine of the SULT2B1 translation initiation codon, an adenine at nucleotide 689 relative to the adenine of the SULT2B1 translation initiation codon, or a thymine at nucleotide 1034 relative to the adenine of the SULT2B1 translation initiation codon, and combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (world wide web at "fr" dot "com" slash "blast"), or the U.S. government's National Center for Biotechnology Information web site (world wide web at "ncbi" dot "nlm" dot "nih" dot "gov" slash "blast" slash "executables"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO:1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a SULT2B1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis *Genetic Engineering News* 12(9):1 (1992); Guatelli et al (1990) *Proc. Natl. Acad. Sci. USA,* 87:1874-1878; and Weiss (1991) *Science* 254:1292.

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequence depicted in FIG. 1, 2A, or 2C can be mutated using standard techniques including oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Examples of positions that can be modified include those described above.

Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available (e.g., Lipofectin (Invitrogen/Life Technologies); Fugene (Roche, Indianapolis, Ind.); and SuperFect (Qiagen, Valencia, Calif.)).

SULT2B1 Polypeptides

Isolated SULT2B1 polypeptides of the invention include an amino acid sequence variant relative to the reference SULT2B1 polypeptide (FIGS. 3B and 3D, and GenBank Accession Nos. U92314 and 92315). The term "isolated" with respect to a SULT2B1 polypeptide refers to a polypeptide that has been separated from cellular components by which it is naturally accompanied. Typically, a SULT2B1 polypeptide is isolated when it is at least 60% (e.g., 65%, 70%, 75%, 80%, 90%, 95%, or 99%), by weight, free from proteins and naturally-occurring organic molecules with which it is naturally associated. In general, an isolated polypeptide will yield a single major band on a non-reducing polyacrylamide gel.

SULT2B1a polypeptides of the invention include variants at one or more of residues 36, 176, 215, and 330. In particular, a serine residue can be substituted at position 36, an asparagine residue can be substituted at position 176, a histidine residue can be substituted at position 215, or a leucine residue can be substituted at position 330. SULT2B1b polypeptides of the invention include variants at one or more of residues 51, 191, 230, and 345. In particular, a serine residue can be substituted at position 51, an asparagine residue can be substituted at position 191, a histidine residue can be substituted at position 230, or a leucine residue can be substituted at position 345.

In some embodiments, the activity of a SULT2B1 polypeptide is altered relative to the reference SULT2B1 polypeptide. Certain SULT2B1 allozymes can have reduced activity, while other allozymes can have activity that is comparable to the reference SULT2B1 polypeptide. Other allozymes can have increased activity relative to the reference SULT2B1 polypeptide. Activity of SULT2B1 polypeptides can be assessed in vitro using a sulfate acceptor substrate such as DHEA and a donor sulfate molecule such as PAPS. In general, recombinant SULT2B1 polypeptides can be incubated at 37° C. with 0.4 µM $^{35}$S-PAPS and 40 µM DHEA in a potassium phosphate buffer (5 mM, pH 7.5). Reactions can be stopped by precipitating PAPS and SULT2B1 polypeptide (e.g., with barium hydroxide, barium acetate, and zinc sulfate). After centrifugation of the reaction, radioactivity in the supernatant can be assessed. SULT2B1 activity is expressed as nmoles of sulfate conjugated product formed per hour of incubation. See, Campbell et al (1987) *Biochem. Pharmacol.* 36:1435-1446.

Other biochemical properties of allozymes, such as apparent $K_m$ values, also can be altered relative to the reference SULT2B1 polypeptide. Apparent $K_m$ values can be calculated, for example, by using the method of Wilkinson with a computer program written by Cleland. Wilkinson (1961) *Biochem. J.* 80:324-332; and Cleland (1963) *Nature* 198:463-365. As described herein, the apparent $K_m$ values for DHEA vary among the allozymes tested.

Isolated polypeptides of the invention can be obtained, for example, by extraction from a natural source (e.g., liver tissue), chemical synthesis, or by recombinant production in a host cell. To recombinantly produce SULT2B1 polypeptides, a nucleic acid sequence containing a SULT2B1 nucleotide sequence variant can be ligated into an expression vector and used to transform a bacterial or eukaryotic host cell (e.g., insect, yeast, or mammalian cells). In general, nucleic acid constructs include a regulatory sequence operably linked to a sulfotransferase nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors (Amersham Biosciences Corp., Piscataway, N.J.) that produce fusion proteins with glutathione S-transferase (GST). Transformed *E. coli* typically are grown exponentially, and then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express SULT2B1 variant polypeptides. A nucleic acid encoding a polypeptide of the invention can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Mammalian cell lines that stably express SULT2B1 variant polypeptides can be produced by using expression vectors with the appropriate control elements and a selectable marker. For example, the eukaryotic expression vectors pCR3.1 (Invitrogen) and p91023(B) (see Wong et al. (1985) *Science* 228:810-815) are suitable for expression of sulfotransferase variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines can be selected, e.g., by antibiotic resistance to G418, kanamycin, or hygromycin. Alternatively, amplified sequences can be ligated into a mammalian expression vector such as pcDNA3 (Invitrogen) and then transcribed and translated in vitro using wheat germ extract or rabbit reticulocyte lysate.

SULT2B1 variant polypeptides can be purified by known chromatographic methods including DEAE ion exchange, gel filtration, and hydroxylapatite chromatography. See, e.g., Van Loon and Weinshilboum (1990) *Drug Metab. Dispos.* 18:632-638; and Van Loon et al. (1992) *Biochem. Pharmacol* 44:775-785. SULT2B1 polypeptides can be "engineered" to contain an amino acid sequence that allows the polypeptide to be captured onto an affinity matrix. For example, a tag such as c-myc, hemagglutinin, polyhistidine, or Flag™ (Kodak) can be used to aid polypeptide purification. Such tags can be inserted anywhere within the polypeptide including at either the carboxyl or amino terminus. Other fusions that can be useful include enzymes that aid in the detection of the polypeptide, such as alkaline phosphatase. Immunoaffinity chromatography also can be used to purify SULT2B1 polypeptides.

Non-Human Mammals

The invention features non-human mammals that include SULT2B1 nucleic acids of the invention, as well as progeny and cells of such non-human mammals. Non-human mammals include, for example, rodents such as rats, guinea pigs, and mice, and farm animals such as pigs, sheep, goats, horses and cattle. Non-human mammals of the invention can express a SULT2B1 nucleotide sequence variant in addition to an endogenous SULT2B1 nucleic acid (e.g., a transgenic non-human that includes a SULT2B1 nucleic acid molecule randomly integrated into the genome of the non-human mammal). Alternatively, an endogenous SULT2B1 nucleic acid can be replaced by a SULT2B1 nucleic acid molecule containing a SULT2B1 nucleotide sequence variant through homologous recombination. See, Shastry (1998) *Mol. Cell. Biochem.* 181:163-179, for a review of gene targeting technology.

In one embodiment, non-human mammals are produced that lack an endogenous SULT2B1 nucleic acid (i.e., a knockout), and then a SULT2B1 variant nucleic acid of the invention is introduced into the knockout non-human mammal. Nucleic acid constructs used for producing knockout non-human mammals can include a nucleic acid sequence encoding a selectable marker, which generally is used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems can include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells since the zygote is the mitotic progenitor of all cells in the embryo. Since targeted insertion of a knockout construct is a relatively rare event, it typically is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This generally is accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous SULT2B1 nucleic acid. That is, cultured ES cells can be transformed with a knockout construct and cells selected in which the SULT2B1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Sections 9.37-9.52 of Sambrook et al., *Molecular Cloning A Laboratory Manual*, second edition, Cold Spring Harbor Press, Plainview; NY, 1989.

To generate a knockout animal, ES cells having at least one inactivated SULT2B1 allele can be incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals whose cells (including germ cells) carry the inactivated SULT2B1 allele. If the original ES cell was heterozygous for the inactivated SULT2B1 allele, several of these animals can be bred with each other in order to generate animals homozygous for the inactivated allele.

Alternatively, direct microinjection of DNA into eggs can be used to avoid the manipulations required to generate an animal from a cultured cell. Fertilized eggs are "totipotent," i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the SULT2B1 gene is interrupted by a coding region that produces a detectable (e.g., fluorescent) gene product, then the injected eggs can be cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous SULT2B1 gene and express a SULT2B1 nucleic acid of the invention, and then fused with enucleated oocytes. After activation of the oocytes, the eggs are cultured to the blastocyst stage, and implanted into a recipient. See, Cibelli et al (1998) *Science* 280:1256-1258. Adult somatic cells including, for example, cumulus cells and mammary cells, can be used to produce animals such as mice and sheep, respectively. See, for example, Wakayama et al. (1998) *Nature* 394:369-374; and Wilmut et al (1997) *Nature* 385:810-813. Nuclei can be removed from genetically modified adult somatic cells and transplanted into enucleated oocytes. After activation, the eggs can be cultured to the 2-8 cell stage, or to the blastocyst stage, and implanted into a suitable recipient. Wakayama, T. et al, 1998, supra.

Non-human mammals of the invention such as mice can be used to screen, for example, toxicity of compounds that are substrates for SULT2B1 polypeptides, drugs that alter SULT2B1 polypeptide activity, or for carcinogenesis. For example, SULT2B1 polypeptide activity or toxicity can be assessed in a first group of such non-human mammals in the presence of a compound, and compared with SULT2B1 polypeptides activity or toxicity in a corresponding control group in the absence of the compound. As used herein, suitable compounds include biological macromolecules such as an oligonucleotide (RNA or DNA) or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally and parenterally. For example, the compound can be administered parenterally through inhalation, or by intranasal, intravascular, intramuscular, or subcutaneous administration. Enteral routes include sublingual and oral administration. Compounds can be prepared for parenteral administration in the form of liquid solutions or suspensions; for oral administration in the form of tablets or capsules; or for intranasal administration in the form of powders, nasal drops, or aerosols.

Compounds can be prepared for other routes of administration using standard techniques. Test compounds can be mixed with non-toxic excipients or carriers before administration. Inhalation formulations can include aqueous solutions containing, for example, polyoxyethylene-9-lauryl ether, glycocholate, or deoxycholate. Other formulations may contain sterile water or saline, or polyalkylene glycols such as polyethylene glycol.

Detecting SULT2B1 Sequence Variants

SULT1B1 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al (1995) *Nat. Biotechnol.* 15:33-39), denaturing high performance liquid chromatography (DHPLC, Underhill et al (1997) *Genome Res.* 7:996-1005), infrared matrix-assisted laser desorption/ionization (IR-MALDI) mass spectrometry (WO 99/57318), and combinations of such methods.

Genomic DNA generally is used in the analysis of SULT2B1 nucleotide sequence variants. Genomic DNA typically is extracted from a biological sample such as a peripheral blood sample, but also can be extracted from other biological samples, including tissues (e.g., mucosal scrapings of the lining of the mouth or from renal or hepatic tissue). Standard methods can be used to extract genomic DNA from a blood or tissue sample, including, for example, phenol extraction. Alternatively, genomic DNA can be extracted with kits such as the QIAamp® Tissue Kit (Qiagen, Valencia, Calif.), Wizard® Genomic DNA purification kit (Promega, Madison, Wis.) and the A.S.A.P.™ Genomic DNA isolation kit (Boehringer Mannheim, Indianapolis, Ind.).

Typically, an amplification step is performed before proceeding with the detection method. For example, exons or introns of the SULT1B1 gene can be amplified and then directly sequenced. Dye primer sequencing can be used to increase the accuracy of detecting heterozygous samples.

Allele specific hybridization also can be used to detect SULT1B1 nucleotide sequence variants, including complete haplotypes of a mammal. See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions can be selected such that a nucleic acid probe can specifically bind to the sequence of interest, e.g., the SULT2B1 nucleic acid molecule containing a particular SULT2B1 nucleotide sequence variant. Such hybridizations typically are performed under high stringency, as some nucleotide sequence variants include only a single nucleotide difference. High stringency conditions can include, for example, the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For SULT2B1 nucleotide sequence variants that introduce a restriction site, restriction digest with the particular restriction enzyme can differentiate the alleles. For SULT2B1 nucleotide sequence variants that do not alter a common restriction site, mutagenic primers can be designed that introduce a restriction site when the variant allele is present or when the wild type allele is present. A portion of a SULT2B1 nucleic acid can be amplified using the mutagenic primer and a wild type primer, followed by digest with the appropriate restriction endonuclease.

Certain variants, such as insertions or deletions of one or more nucleotides, can change the size of the DNA fragment encompassing the variant. The insertion or deletion of nucleotides can be assessed by amplifying the region encompassing the variant and determining the size of the amplified products in comparison with size standards. For example, a region of a SULT2B1 nucleic acid can be amplified using a primer set from either side of the variant. One of the primers typically is labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, SULT2B1 allozymes can be detected by antibodies that have specific binding affinity for the particular allozymes. SULT2B1 allozymes can be produced in various ways, including recombinantly, as discussed above. Host animals such as rabbits, chickens, mice, guinea pigs and rats can be immunized by injection of a particular SULT2B1 allozyme. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a SULT2B1 allozyme and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today* 4:72; Cote et al. (1983) *Proc. Natl. Acad. Sci. USA* 80:2026), and the EBV-hybridoma technique (Cole et al., *Monoclonal Antibodies and Cancer Therapy*, Alan R. Liss, Inc., pp. 77-96, 1983). Such antibodies can be of any immunoglobulin class, including IgG, IgM, IgE, IgA, IgD, and any subclass thereof. The hybridoma producing the monoclonal antibodies of the invention can be cultivated in vitro and in vivo.

Antibody fragments that have specific binding affinity for a SULT2B1 allozyme can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al, *Science*, 246:1275 (1989). Once produced, antibodies or fragments thereof are tested for recognition of SULT2B1 allozymes by standard immunoassay methods including ELISA techniques, radioimmunoassays and Western blotting. See, *Short Protocols in Molecular Biology*, Chapter 1, Green Publishing Associates and John Wiley & Sons, edited by Ausubel et al., 1992.

Methods

As a result of the present invention, it is possible to determine sulfonator status of a subject (e.g., a mammal such as a human). "Sulfonator status" refers to the ability of a subject to transfer a sulfate group to a substrate (e.g., DHEA). Sulfonator status of a subject can be determined by, for example, measuring the level of sulfotransferase (e.g., SULT2B1) activity in the subject using, for example, the methods described herein. Alternatively, sulfonator status can be evaluated by determining whether a sulfotransferase nucleic acid sequence (e.g., the SULT2B1 nucleic acid sequence) of a subject contains one or more variants (e.g., one or more variants that are correlated with increased or decreased sulfotransferase activity). A variant that results in decreased or increased SULT2B1 activity, for example, can be said to result in "reduced" or "enhanced" sulfonator status, respectively. In some embodiments, the variant profile of a subject can be used to determine the sulfonator status of the subject.

"Variant profile" refers to the presence or absence of a plurality (e.g., two or more) of SULT2B1 nucleotide sequence variants or SULT2B1 amino acid sequence variants. For example, a variant profile can include the complete SULT2B1 haplotype of the mammal (e.g., see Table 5) or can include the presence or absence of a set of particular non-synonymous SNPs (e.g., single nucleotide substitutions that alter the amino acid sequence of a SULT2B1 polypeptide). In one embodiment, the variant profile includes detecting the presence or absence of two or more non-synonymous SNPs (e.g., 2, 3, or 4 non-synonymous SNPs described herein. There may be ethnic-specific pharmacogenetic variation, as certain of the nucleotide and amino acid sequence variants described herein were detected solely in African-American subjects. In addition, the variant profile can include detecting the presence or absence of any type of SULT2B1 SNP together with any other SULT2B1 SNP (e.g., a polymorphism pair or a group of polymorphism pairs). Such polymorphism pairs include, without limitation, the pairs described in Table 4.

Sulfotransferase activity of an enzyme such as SULT2B1 can be measured using, for example, in vitro methods such as those described herein. As used herein, the term "reduced sulfonator status" refers to a decrease (e.g., a 5%, 10%, 15%, 20%, 25%, 30%, 40%, 50%, 60%, 70%, 75%, 80%, 90%, 95%, or 100% decrease) in sulfotransferase activity (e.g., SULT2B1 activity) of a subject, as compared to a control level of sulfotransferase activity. Similarly, the term "enhanced sulfonator status" refers to an increase (e.g., a 5%, 10%, 15%, 20%, 25%, 30%, 40%, 50%, 60%, 70%, 75%, 80%, 90%, 95%, 100%, or more than 100% increase) in sulfotransferase activity of a subject, as compared to a control level of sulfotransferase activity. A control level of sulfotransferase activity can be, for example, an average level of sulfotransferase activity in a population of individuals. In one embodiment, the population includes individuals that do not contain particular SULT2B1 nucleotide sequence variants or particular SULT2B1 amino acid sequence variants (e.g., particular variants that affect sulfonator status). Alternatively, a control level of sulfotransferase activity can refer to the level of sulfotransferase activity in a control subject (e.g., a subject that does not contain a SULT2B1 nucleic acid containing a variant).

In some embodiments, evaluation of sulfonator status can be used in diagnostic assays to determine whether a particular therapy may be useful in an individual (e.g., whether a subject can metabolize a particular drug). Sulfation typically detoxifies compounds, since the resulting ionized, organic sulfates are more readily excreted than the unsulfated compounds. Furthermore, functional groups that may interact with biological macromolecules such as nucleic acids or proteins can be masked by a sulfate moiety. SULT2B1 plays a role in the modification of molecules including, for example, DHEA, cholesterol, Minoxidil, pregnenolone, epiandrosterone, and androstenediol. Such compounds may be readily metabolized in a subject with enhanced sulfonator status, while an individual with reduced sulfonator status may have reduced capacity to metabolize such compounds. Thus, detecting sulfotransferase nucleic acid and amino acid sequence variants can facilitate the prediction of therapeutic efficacy and toxicity of drugs on an individual basis. As used herein, a "therapeutically effective" dose of a compound is a dose that results in the desired effect of the compound, while minimizing deleterious effects that might result from the compound If it is not metabolized and eliminated from the body.

Furthermore, evaluating the sulfonator status of an individual can be useful for estimating dosages of particular therapies to be administered to the individual. For example, the sulfonator status of a subject may affect the metabolism of molecules such as DHEA. Thus, an individual with decreased SULT2B1 activity might receive greater benefit from an average dose of DHEA as compared to an individual with a greater (e.g., "normal") level of SULT2B1 activity. Conversely, a female using the oral contraceptive ethinyl estradiol with decreased SULT2B1 activity may have higher circulating estrogen concentrations, a known risk factor for vascular conditions such as heart attack or stroke.

In further embodiments of the invention, sulfonator status can be linked to predisposition to a particular condition (e.g., a heart condition, cancer, or a dermal disease). Predisposition refers to a relative greater risk for a heart condition such as heart attack or stroke, a cancer such as testicular cancer, or a dermal disease such as ichthyosis. Additional risk factors including, for example, family history of heart disease or cancer and other genetic factors can be considered when determining risk. Predisposition of a subject to a heart condition, cancer, or a dermal disease can be determined based on the presence or absence of a single sulfotransferase sequence variant or based on a variant profile.

Articles of Manufacture

The invention also provides articles of manufacture that include populations of isolated SULT2B1 nucleic acid molecules or SULT2B1 polypeptides immobilized on a substrate. Suitable substrates can provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different SULT2B1 nucleotide or SULT2B1 amino acid sequence variant. Such articles of manufacture can include two or more nucleotide or amino acid sequence variants, or can include all of the sequence variants known for SULT2B1. Furthermore, nucleic acid molecules containing sequence variants for other sulfotransferases, such as SULT1A1, SULT1A2, SULT1A3, and SULT1A2, can be included on the substrate. See, WO 99/64630 and WO 00/20605 for a description of other SULT1A1, SULT1A2, SULT1A3, and SULT1A2 sequence variants.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules typically are about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and any hybridization can be detected. Typically, the amplified product is labeled to facilitate detection of hybridization. See, for example, Hacia et al. (1996) *Nature Genet.* 14:441-447; and U.S. Pat. Nos. 5,770,722 and 5,733,729.

The invention will be further described in the following examples, which do not limit the scope of the invention described in the claims.

EXAMPLES

Example 1

Methods and Materials: PCR Amplification and DNA Sequencing

Genomic DNA from 60 African American blood donors and 60 Caucasian blood donors was obtained from Coriell Cell Repositories (Camden, N.J.). The DNA was used as a template in a PCR with SULT2B1-specific primers. The seven exons in the SULT2B1 gene were amplified from each of the 120 DNA samples using primers that flanked the exons and that would produce amplification products 400-500 bp in length. Amplification of the entire gene required seven separate reactions for each DNA sample. The hybridization location of each primer was chosen to avoid repetitive sequence and to ensure amplification specificity. All forward primers contained the M13 forward sequence, and all reverse primers contained the M13 reverse sequence for use in dye primer DNA sequencing. The sequences and locations of each primer within the gene are listed in Table 1 ("F" represents forward; "R", reverse; "U", upstream; "D", downstream; "I", intron; "FR", flanking region; and "UTR", untranslated region).

Following amplification, the products from each reaction were sequenced using dye primer DNA sequencing chemistry to identify heterozygous bases. DNA sequencing was performed in the Mayo Clinic Molecular Biology Core Facility with an Applied Biosystems Model 377 DNA sequencers and BigDye™ (Perkin Elmer, Foster City, Calif.) dye primer sequencing chemistry. In all cases, both DNA strands were sequenced.

DNA sequence analysis: The seven separate SULT1B1 PCR amplifications performed for each of the 120 individual human genomic DNA samples described above generated a total of approximately 600,000 bp of sequence. The DNA chromatograms for this sequence were analyzed both visually and using PolyPhred 3.0, Consed 8.0, and GCG 10.0 software. All sequences were compared to the SULT2B1 gene sequences of GenBank accession number NM_030640.

COS-1 cell expression: A plurality of different SULT2B1 expression constructs are made using the pCR3.1 expression vector. All but one of the constructs are designed to express SULT2B1 allozymes, while the remaining construct is designed to express a wild type SULT2B1 polypeptide. All SULT2B1 cDNA sequences containing SULT2B1 nucleotide sequence variants used to create the expression constructs are created by site directed mutagenesis using the method described by Ho et al. (1989) *Gene* 77:51-59. Each SULT2B1 cDNA is amplified by PCR and subcloned into the eukaryotic expression vector pCR3.1 (Promega, Madison, Wis.). After subcloning, all inserts are sequenced to assure that no spurious nucleotide point mutations have been introduced during the PCR amplifications. COS-1 cells are transfected with these expression constructs by the TransFast™ reagent (Promega, Madison, Wis.) as suggested by the manufacturer (i.e., using a 1:1 charge ratio). As a control, a transfection also is performed with "empty" pCR3.1, i.e., vector lacking an insert, to make it possible to correct for endogenous COS-1 cell SULT activity. The control plasmid pSV-β-galactosidase (Promega) is cotransfected with each SULT2B1 construct to make it possible to correct for transfection efficiency. Two independent transfections, each consisting of three separate plates, are performed with each of the expression constructs. After 48 hours in culture, the transfected cells are harvested and high speed supernatant (HSS) cytosol preparations are prepared as described by Wood et al (1994) *Biochem. Biophys. Res. Commun.* 198:1119-1127. Aliquots of these cytosol preparations are stored at −80° C. prior to assay.

Enzyme Assays: β-galactosidase activity in each of the COS-1 HSS preparations is measured with the β-galactosidase Enzyme Assay System (Promega, Madison, Wis.). These HSS preparations of recombinant SULT2B1 allozymes are used for the activity studies without any further purification. The protein concentration of each recombinant protein preparation is determined by the dye-binding method of Bradford with bovine serum albumin (BSA) as a standard.

SULT2B1 enzyme activity is measured with an assay that involves sulfate conjugation of a sulfate acceptor substrate, DHEA, in the presence of the sulfate donor 3'-phosphoadenosine-5'-phosphosulfate (PAPS). See, Campbell et al. (1987) *Biochem. Pharmacol.* 36:1435-1446. Briefly, 0.4 μM $^{35}$S-PAPS and a HSS preparation are reacted with 40 μM DHEA in 5 mM potassium phosphate buffer at pH 7.5. Blanks are samples that did not contain DHEA. Cytosol from COS-1 cells that have been transfected with empty pCR3.1 are used to correct for endogenous SULT activity. Because SULTs display profound substrate inhibition, DHEA concentrations that range from 100 pM to 1 mM are tested with each recombinant allozyme to ensure that the assays are performed at DHEA concentrations that yield maximal activity for that allozyme. Enzyme activity is expressed as nanomoles (nmoles) of sulfate conjugated product formed per hour of incubation. Apparent $K_m$ values for PAPS are determined in the presence of 5 μM DHEA with six PAPS concentrations that vary from 0.0625 μM to 2 μM.

Data Analysis: Apparent $K_m$ values are calculated by using the method of Wilkinson with a computer program written by Cleland. See, Wilkinson supra; and Cleland supra. Statistical comparisons of data are performed by ANOVA with the StatView program, version 4.5 (Abacus Concepts, Inc., Berkeley, Calif.). Linkage analysis was performed after all DNA samples had been genotyped at each of the 6 polymorphic sites observed. D' values, a quantitative method for reporting linkage data that is independent of allele frequency (Hartl and Clark, *Principles of Population Genetics*, 3$^{rd}$ ed. (1997) Sinauer Associates, Inc., (Sunderland, Mass.), pp. 96-106; and Hedrick, *Genetics of Populations*, 2$^{nd}$ ed. (2000) Jones and Bartlett (Sudbury, Mass.), pp. 396-405), were then calculated. The genotype data also were used to assign inferred haplotypes using a program based on the E-M algorithm (Long et al. (1995) *Am. J. Hum. Genet.* 56:799-810; and Excoffier and Slatkin (1995) *Mol. Biol. Evol.* 12:921-927). Unambiguous haplotype assignment also was possible on the basis of genotype for samples that contained no more than one heterozygous polymorphism.

Western blot analysis: Quantitative Western blot analysis is performed with recombinant SULT2B1 protein. The quantity of cytosol loaded on the gel for each allozyme is adjusted so that each lane contains an equal quantity of β-galactosidase activity and thus gel loading is corrected for variation in transfection efficiency. Properties of the antibody used to detect the SULT2B1 protein have been described elsewhere. Bound antibody is detected using the ECL system (Amersham Biosciences). The Ambis densitometric system is used to quantitate immunoreactive protein in each lane, and those data are expressed as a percent of the intensity of the control wild type SULT2B1 protein band on that gel.

Figure 4:
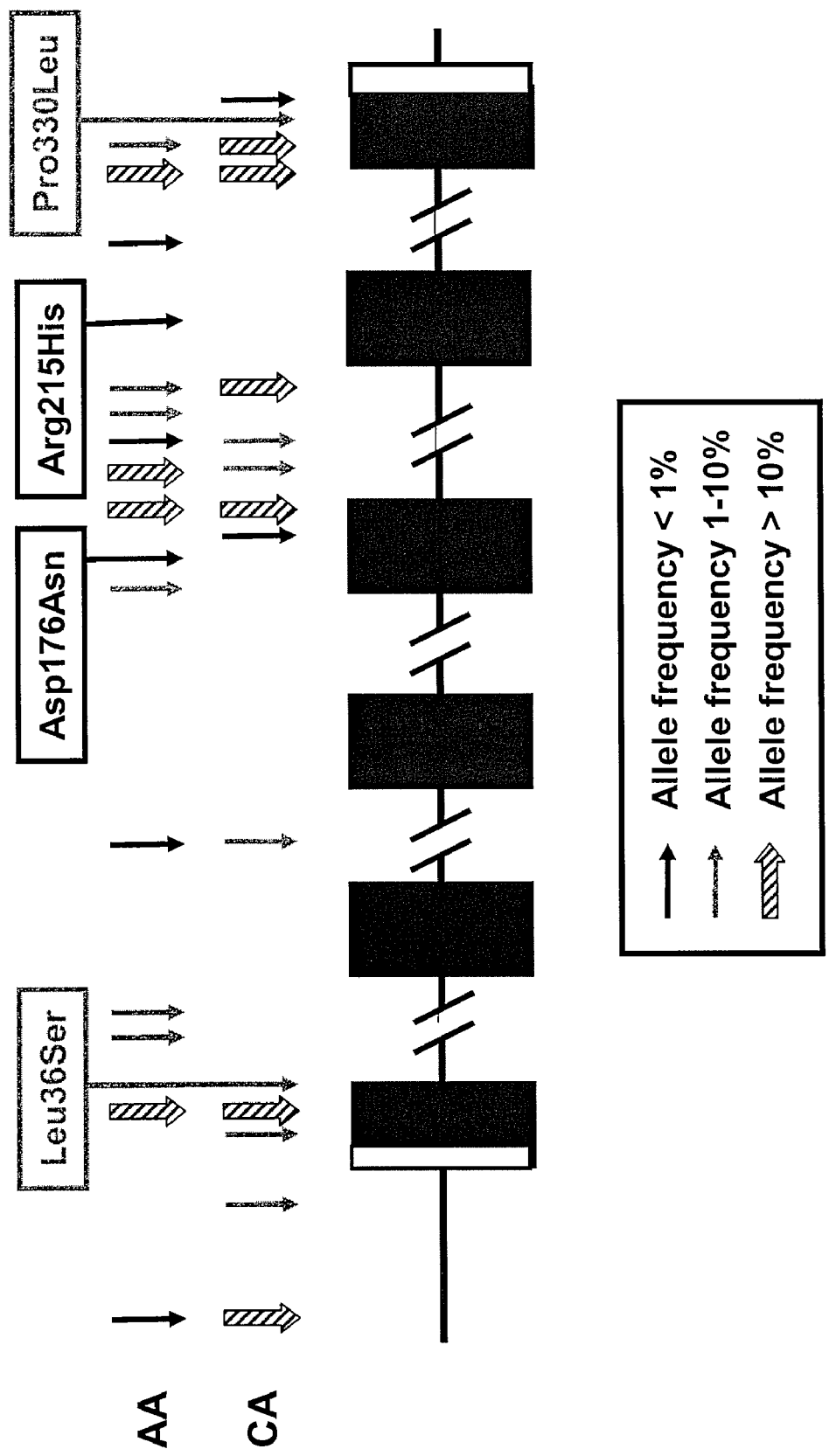
FIG. 4 is a schematic of the locations of polymorphisms within the SULT2B1 amino acid sequence in Caucasian Americans (CA) and African Americans (AA). Residue numbers are given with respect to the SULT2B1a sequence.

(UTR), and flanking regions (FR) are numbered relative to the adenine in the SULT2B1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1). Two of the 17 SNPs altered the encoded amino acid (i.e., a non-synonymous SNP), resulting in two different SULT2B1 allozymes. One of the two variants appeared to be "common" (frequency >1%, Table 2) among the 60 African American samples. The same two variants were not detected among the 60 Caucasian samples. Locations of the polymorphisms are shown in FIG. 4.

The average number of polymorphisms present in the gene overall, within the ORF, and outside the ORF was 4.2, 2.2, and 4.8 per kb sequenced, respectively, in the African American samples (Table 3). The average number of polymorphisms present in the gene overall and within the ORF was 2.8, 0, and 3.7 per kb sequenced, respectively, in the Caucasian samples (Table 3). For purposes of comparison, Table 3 also includes data from a large study of polymorphism frequencies in 74 human genes (Halushka et al. (1999) *Nat. Genet.* 22:239-247). Because Halushka et al studied a slightly smaller number of samples (74 versus the 120 described), low frequency polymorphisms that would not have been detected

TABLE 1

PCR primers used for resequencing SULT2B1

| Primer Name | Primer Location | Primer Sequence Gene Specific Primer-3' | SEQ ID NO: |
|---|---|---|---|
| AF(-535) M13 | 5'-FR Exon A | TGTAAAACGACGGCCAGTAGGATGAGAGCCAGGTTC | 19 |
| AR(-155) M13 | 5'-FR Exon A | CAGGAAACAGCTATGACCCTGTAATCCCAGCACTTTG | 20 |
| AF(-116) M13 | 5'-FR Exon A | TGTAAAACGACGGCCAGTGGGACAGTGTCACCAC | 21 |
| I1AR81 M13 | Intron 1A | CAGGAAACAGCTATGACCCTTCTCTATGTGCCTTTCC | 22 |
| BF(-148) M13 | 5'-FR Exon B | TGTAAAACGACGGCCAGTAGCACCAGACGCCAGGA | 23 |
| I1R163 M13 | Intron 1B | CAGGAAACAGCTATGACCCACACTGGATGCCCCAG | 24 |
| I1F(-100) M13 | Intron 1B | TGTAAAACGACGGCCAGTGGTGGCAAATTGCTCAATAA | 25 |
| I2R56 M13 | Intron 2 | CAGGAAACAGCTATGACCATTACCCCATACACCCATGC | 26 |
| I2F(-87) M13 | Intron 2 | TGTAAAACGACGGCCAGTAGGGGTCTCCAGGGCA | 27 |
| I3R167 M13 | Intron 3 | CAGGAAACAGCTATGACCTCCGTCTCTTCTTTCTCCTG | 28 |
| I3F(-27) M13 | Intron 3 | TGTAAAACGACGGCCAGTCTCACCCCACTTGTCCCT | 29 |
| I4R195 M13 | Intron 4 | CAGGAAACAGCTATGACCAGCCTGCTGTGTGGT | 30 |
| I4F(-89) M13 | Intron 4 | TGTAAAACGACGGCCAGTGTTAGGACCCAGACATG | 31 |
| I5R108 M13 | Intron 5 | CAGGAAACAGCTATGACCAATGTTACAGCTGGGTGAG | 32 |
| I5F(-131) M13 | Intron 5 | TGTAAAACGACGGCCAGTGGACGGTGTTTCTGGC | 33 |
| DR81 M13 | Exon 6 | CAGGAAACAGCTATGACCGGTGTGGTGAGGATTCT | 34 |

Underlined nucleotides indicate M13 tag

Example 2

SULT2B1 Polymorphisms

Sequencing of the 5' and 3' untranslated sequences, exons, and introns of the SULT2B1 nucleic acid revealed 21 SNPs (Table 2). Polymorphisms in exons, untranslated regions by Halushka et al. have been eliminated because of their lower sample number. The genetic variation present within the SULT1B1 sequence was very similar to average values observed in the 74 genes sequenced by Halushka et al. The data in Table 3 also are presented by gene region, with "UTR" representing both exons encoding cDNA untranslated regions and 5'- and 3'-flanking regions.

TABLE 2

Human SULT2B1 sequence variants

| Polymorphism Position | Location In Gene | WT Sequence Nucleotide | Variant Sequence Nucleotide | AA | CA |
|---|---|---|---|---|---|
| -21b | 5'-FR Exon 1b | C | T | 0.000 | 0.034 |
| 14b | Exon 1b | C | T | 0.000 | 0.011 |
| -183a | 5'-FR Exon 1a | C | T | 0.008 | 0.100 |
| 75 | Exon 1a | C | T | 0.167 | 0.096 |
| 107* | Exon 1a | T | C | 0.000 | 0.018 |
| I1a22 | Intron 1a | C | T | 0.018 | 0.000 |
| I1a23 | Intron 1a | G | A | 0.018 | 0.000 |
| I2(-10) | Intron 2 | C | T | 0.008 | 0.042 |
| 525 | Exon 4 | C | T | 0.025 | 0.000 |
| 526* | Exon 4 | G | A | 0.008 | 0.000 |
| 555 | Exon 4 | G | A | 0.000 | 0.008 |
| 592 | Exon 4 | C | T | 0.263 | 0.350 |
| I4(88) | Intron 4 | C | A | 0.102 | 0.083 |
| I4(94) | Intron 4 | G | A | 0.008 | 0.042 |
| I4(172) | Intron 4 | A | G | 0.017 | 0.000 |
| I4(-41) | Intron 4 | C | T | 0.050 | 0.200 |
| 644* | Exon 5 | G | A | 0.008 | 0.000 |
| I5(3) | Intron 5 | G | A | 0.008 | 0.000 |
| 789 | Exon 6 | C | T | 0.225 | 0.417 |
| 903 | Exon 6 | C | T | 0.058 | 0.192 |
| 989* | Exon 6 | C | T | 0.000 | 0.025 |
| 1009* | Exon 6 | AGCCCC | – | 0.000 | 0.008 |

*Non-synonymous

TABLE 3

SULT2B1 polymorphism frequencies

Polymorphisms per kb

| | SULT1B1 | | |
|---|---|---|---|
| | African American | Caucasian | 74 Human Genes |
| Gene(s) | 1 | 1 | 74 |
| Samples | 60 | 60 | 75 |
| Min. Allele Freq. | 0.8 | 0.8 | 0.68% |
| Overall | 4.4 | 4.1 | 4.6 |
| Coding | 6.2 | 8.0 | 4.4 |
| Noncoding | 3.6 | 2.4 | 5.9 |
| UTRs | 0.8 | 1.6 | 4.4 |
| Introns | 6.5 | 3.3 | 6.0 |

Example 3

Linkage Disequilibrium Analysis and Haplotype Analysis

Linkage disequilibrium analysis was performed after all of the DNA samples had been genotyped at each of the 15 polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate d' values, a method for reporting linkage data that is independent of sample size. All pairwise combinations with a linkage disequilibrium greater than or equal to 1% are shown in Table 4.

The genotype data also were used for haplotype analysis (Table 5). Six unequivocal haplotypes were identified by these studies. As shown in Table 5, the haplotype analysis accounted for 10% and 19% of all samples based on these unequivocal haplotypes for DNA samples from African- American and Caucasian-American subjects, respectively. The unequivocal haplotypes included three that were common to both ethnic groups and three others that were ethnic-specific for Caucasian-American subjects.

TABLE 4

SULT2B1 linkage disequilibrium analysis

| Polymorphism Pair AA | | d' Value | $\chi^2$ Value |
|---|---|---|---|
| −183 | I4(−41) | 1 | 0.029 |
| −183 | 903 | 1 | 0.035 |
| I2(−10) | I4(94) | 1 | 0.0014 |
| 525 | I4(88) | 1 | 0.000284 |
| 592 | I4(88) | −1 | 0.0625 |
| 592 | 789 | −1 | 0.012 |
| I4(−41) | 903 | 1 | 0 |

TABLE 4-continued

SULT2B1 linkage disequilibrium analysis

| Polymorphism Pair CA | | d' Value | P Value |
|---|---|---|---|
| −183 | 107 | 1 | 0.009334 |
| −183 | 592 | 0.8077 | 0.006727 |
| −183 | I4(−41) | 1 | 0 |
| −183 | 789 | −1 | 0.041 |
| −183 | 903 | 1 | 0 |
| 107 | 903 | 1 | 0.046 |
| 14 | 858 | 1 | 0.0014 |
| I2(−10) | I4(94) | 1 | 0 |
| 592 | I4(88) | −1 | 0.026 |
| 592 | 789 | −1 | 0 |
| I4(88) | 789 | −1 | 0.015 |
| I4(−41) | 789 | −1 | 0.001 |
| I4(−41) | 903 | 1 | 0 |
| 789 | 903 | −1 | 0.002 |
| 789 | 989 | 1 | 0.046 |

TABLE 5

SULT2B1 haplotype analysis

| AA Frequency | Caucasian Frequency | −139 | I1 (80) | I3 (131) | 433 | I4 (−15) | I5 (58) | 907 | 1059 |
|---|---|---|---|---|---|---|---|---|---|
| 0.046 | 0.019 | WT | V | WT | WT | WT | WT | V | WT |
| 0.034 | 0.053 | WT | WT | WT | WT | WT | V | WT | V |
| 0.021 | 0.021 | WT | V | WT | WT | V | WT | WT | WT |
| 0.000 | 0.0583 | V | WT | WT | WT | V | V | WT | V |
| 0.000 | 0.017 | WT | WT | WT | WT | V | V | WT | V |
| 0.000 | 0.017 | WT | WT | V | WT | WT | WT | V | WT |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated nucleic acid molecule consisting of: (a) twenty to 100 contiguous nucleotides of SEQ ID NO: 15, wherein said nucleic acid molecule includes at least one nucleotide selected from positions 482, 901, and 1364 of SEQ ID NO: 15, with the proviso that the nucleotide at position 482 is cytosine, the nucleotide at position 901 is adenine, and/or the nucleotide at position 1364 is thymine; or (b) the complement of (a).

2. The isolated nucleic acid molecule of claim 1, wherein said isolated nucleic acid molecule is 20 to 50 nucleotides in length.

3. A vector comprising the nucleic acid molecule of claim 1.

4. The vector of claim 3, wherein said nucleic acid molecule is 20 to 50 nucleotides in length.

5. An article of manufacture comprising a substrate, wherein said substrate comprises the isolated nucleic acid molecule of claim 1.

6. An isolated nucleic acid molecule consisting of: a) twenty to 100 contiguous nucleotides of SEQ ID NO:15, wherein said nucleic acid molecule includes one or more of nucleotides 482, 901, and 1364 of SEQ ID NO:15, with the proviso that the nucleotide at position 482 is cytosine, the nucleotide at position 901 is adenine, and/or the nucleotide at position 1364 is thymine; or b) the complement of a), and, with respect to a) or b), a label.

7. The isolated nucleic acid molecule of claim 6, wherein said label is a fluorescent moiety.

8. The isolated nucleic acid molecule of claim 6, wherein said label is biotin.

9. The isolated nucleic acid of molecule of claim 6, wherein said isolated nucleic acid molecule is 20 to 50 nucleotides in length.

10. A vector comprising the nucleic acid molecule of claim 6.

11. The vector of claim 10, wherein said nucleic acid molecule is 20 to 50 nucleotides in length.

12. An article of manufacture comprising a substrate, wherein said substrate comprises the isolated nucleic acid molecule of claim 6.

* * * * *